(12) United States Patent
Kirschman

(10) Patent No.: US 8,945,193 B2
(45) Date of Patent: *Feb. 3, 2015

(54) MINIMALLY INVASIVE SPINAL FACET COMPRESSION SCREW AND SYSTEM FOR BONE JOINT FUSION AND FIXATION

(75) Inventor: David Louis Kirschman, Dayton, OH (US)

(73) Assignee: X-spine Systems, Inc., Miamisburg, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/413,021

(22) Filed: Mar. 6, 2012

(65) Prior Publication Data

US 2012/0197311 A1    Aug. 2, 2012

Related U.S. Application Data

(63) Continuation-in-part of application No. 13/184,862, filed on Jul. 18, 2011.

(60) Provisional application No. 61/365,906, filed on Jul. 20, 2010.

(51) Int. Cl.
```
A61B 17/86    (2006.01)
A61B 17/70    (2006.01)
A61B 17/88    (2006.01)
```

(52) U.S. Cl.
CPC ........... *A61B 17/863* (2013.01); *A61B 17/7064* (2013.01); *A61B 17/8841* (2013.01); *A61B 17/7082* (2013.01); *A61B 17/7098* (2013.01); *A61B 17/861* (2013.01); *A61B 17/864* (2013.01); *A61B 17/8891* (2013.01)
USPC ............ 606/304; 606/307; 606/315; 606/317

(58) Field of Classification Search
USPC .................. 606/300–321; 411/402, 413, 418
See application file for complete search history.

(56) References Cited

U.S. PATENT DOCUMENTS

| | | | |
|---|---|---|---|
| 2,121,193 A | 6/1938 | Hanicke |
| 2,382,019 A | 8/1945 | Miller |
| 2,472,103 A | 6/1949 | Giesen |
| 2,489,870 A | 11/1949 | Dzus |
| 2,570,465 A | 10/1951 | Lundholm |
| 2,801,631 A | 8/1957 | Charnley |
| 3,682,507 A | 8/1972 | Waud |
| 4,059,102 A | 11/1977 | Devas |
| 4,175,555 A | 11/1979 | Herbert |

(Continued)

FOREIGN PATENT DOCUMENTS

| | | |
|---|---|---|
| EP | 1302170 | 4/2003 |
| EP | 1927322 | 6/2008 |
| WO | 2010067363 | 6/2010 |

*Primary Examiner* — Todd Manahan
*Assistant Examiner* — Eric S Gibson
(74) *Attorney, Agent, or Firm* — Jacox, Meckstroth & Jenkins

(57) ABSTRACT

A system comprising a screw element having a generally cylindrical body having a bore or lumen therethrough and a plurality of fenestrations or windows through which biological material may be provided. The system comprises a tool for inserting the biological material into the screw element so that the biological material may extrude through the plurality of fenestrations or windows and through an aperture in the tip of the screw element thereby enabling providing a fusion mass across two adjacent facet bones or a facet joint wherein the screw itself provides both a fixation component and a screw component.

46 Claims, 10 Drawing Sheets

(56) References Cited

U.S. PATENT DOCUMENTS

| | | | |
|---|---|---|---|
| 4,456,005 A | 6/1984 | Lichty | |
| 4,463,753 A | 8/1984 | Gustilo | |
| 4,537,185 A | 8/1985 | Stednitz | |
| 4,640,271 A | 2/1987 | Lower | |
| 4,712,957 A | 12/1987 | Edwards et al. | |
| 4,858,601 A | 8/1989 | Glisson | |
| 4,944,759 A | 7/1990 | Mallory et al. | |
| 4,959,064 A | 9/1990 | Engelhardt | |
| 5,019,079 A | 5/1991 | Ross | |
| 5,047,030 A | 9/1991 | Draenert | |
| 5,116,337 A | 5/1992 | Johnson | |
| 5,120,171 A | 6/1992 | Lasner | |
| 5,180,382 A | 1/1993 | Frigg et al. | |
| 5,226,766 A | 7/1993 | Lasner | |
| 5,259,398 A | 11/1993 | Vrespa | |
| 5,334,204 A | 8/1994 | Clewett et al. | |
| 5,375,956 A * | 12/1994 | Pennig | 411/389 |
| 5,403,136 A | 4/1995 | Mathys | |
| 5,417,533 A | 5/1995 | Lasner | |
| 5,470,334 A | 11/1995 | Ross et al. | |
| 5,492,442 A | 2/1996 | Lasner | |
| 5,505,736 A | 4/1996 | Reimels et al. | |
| 5,536,127 A * | 7/1996 | Pennig | 411/413 |
| 5,562,672 A | 10/1996 | Huebner et al. | |
| 5,593,410 A | 1/1997 | Vrespa | |
| 5,964,768 A | 10/1999 | Huebner | |
| 6,030,162 A | 2/2000 | Huebner | |
| 6,053,916 A * | 4/2000 | Moore | 623/16.11 |
| 6,129,730 A | 10/2000 | Bono et al. | |
| 6,306,140 B1 | 10/2001 | Siddiqui | |
| 6,485,518 B1 | 11/2002 | Cornwall et al. | |
| 6,503,252 B2 | 1/2003 | Hansson | |
| 6,540,747 B1 | 4/2003 | Marino | |
| 6,551,323 B2 | 4/2003 | Doubler et al. | |
| 6,648,893 B2 | 11/2003 | Dudasik | |
| 6,979,163 B2 * | 12/2005 | Brletich et al. | 411/418 |
| 7,223,269 B2 | 5/2007 | Chappuis | |
| 7,452,369 B2 | 11/2008 | Barry | |
| 7,563,275 B2 | 7/2009 | Falahee et al. | |
| 7,608,094 B2 | 10/2009 | Falahee | |
| 7,699,878 B2 | 4/2010 | Pavlov et al. | |
| 7,708,761 B2 | 5/2010 | Petersen | |
| 7,744,630 B2 | 6/2010 | Lancial | |
| 7,749,251 B2 | 7/2010 | Obenchain et al. | |
| 7,837,713 B2 | 11/2010 | Petersen | |
| 7,892,267 B2 | 2/2011 | Lancial et al. | |
| 7,901,439 B2 | 3/2011 | Horton | |
| 7,993,373 B2 | 8/2011 | Hoy et al. | |
| 8,002,812 B2 | 8/2011 | Falahee et al. | |
| 8,021,392 B2 | 9/2011 | Petersen | |
| 8,043,334 B2 | 10/2011 | Fisher et al. | |
| 8,574,273 B2 | 11/2013 | Russell et al. | |
| 2002/0169453 A1 * | 11/2002 | Berger | 606/73 |
| 2003/0208202 A1 | 11/2003 | Falahee | |
| 2004/0087948 A1 | 5/2004 | Suddaby | |
| 2004/0097941 A1 * | 5/2004 | Weiner et al. | 606/72 |
| 2004/0254575 A1 | 12/2004 | Obenchain et al. | |
| 2005/0124993 A1 | 6/2005 | Chappuis | |
| 2005/0149030 A1 | 7/2005 | Serhan et al. | |
| 2005/0152770 A1 | 7/2005 | Tschakaloff et al. | |
| 2005/0267480 A1 | 12/2005 | Suddaby | |
| 2006/0025773 A1 | 2/2006 | Yevmenenko et al. | |
| 2006/0111779 A1 | 5/2006 | Petersen | |
| 2006/0111780 A1 | 5/2006 | Petersen | |
| 2006/0200149 A1 | 9/2006 | Hoy et al. | |
| 2006/0212034 A1 | 9/2006 | Triplett et al. | |
| 2006/0264953 A1 | 11/2006 | Falahee | |
| 2007/0112428 A1 | 5/2007 | Lancial | |
| 2007/0233092 A1 | 10/2007 | Falahee | |
| 2007/0233093 A1 | 10/2007 | Falahee | |
| 2007/0233123 A1 * | 10/2007 | Ahmad et al. | 606/73 |
| 2007/0233125 A1 | 10/2007 | Wahl et al. | |
| 2008/0234758 A1 | 9/2008 | Fisher et al. | |
| 2008/0255618 A1 | 10/2008 | Fisher et al. | |
| 2008/0255619 A1 | 10/2008 | Schneiderman et al. | |
| 2008/0255622 A1 | 10/2008 | Mickiewicz et al. | |
| 2008/0255666 A1 | 10/2008 | Fisher et al. | |
| 2008/0255667 A1 | 10/2008 | Horton | |
| 2008/0262555 A1 | 10/2008 | Assell et al. | |
| 2008/0275454 A1 | 11/2008 | Geibel | |
| 2009/0036926 A1 | 2/2009 | Hestad | |
| 2009/0036927 A1 | 2/2009 | Vestgaarden | |
| 2009/0036986 A1 | 2/2009 | Lancial et al. | |
| 2009/0048675 A1 | 2/2009 | Bhatnagar et al. | |
| 2009/0054903 A1 | 2/2009 | Falahee et al. | |
| 2009/0076551 A1 | 3/2009 | Petersen | |
| 2009/0093851 A1 | 4/2009 | Osman | |
| 2009/0099602 A1 | 4/2009 | Aflatoon | |
| 2009/0105819 A1 | 4/2009 | Barry | |
| 2009/0112264 A1 | 4/2009 | Lins | |
| 2009/0125066 A1 | 5/2009 | Kraus et al. | |
| 2009/0131986 A1 | 5/2009 | Lee et al. | |
| 2009/0163920 A1 | 6/2009 | Hochschuler et al. | |
| 2009/0177205 A1 | 7/2009 | McCormack et al. | |
| 2009/0187219 A1 | 7/2009 | Pachtman et al. | |
| 2009/0192551 A1 | 7/2009 | Cianfrani et al. | |
| 2009/0216273 A1 | 8/2009 | Cox | |
| 2009/0234394 A1 | 9/2009 | Crook | |
| 2009/0234397 A1 | 9/2009 | Petersen | |
| 2009/0248082 A1 | 10/2009 | Crook et al. | |
| 2009/0248085 A1 | 10/2009 | Jacofsky et al. | |
| 2009/0264928 A1 | 10/2009 | Blain | |
| 2009/0270929 A1 | 10/2009 | Suddaby | |
| 2009/0275954 A1 | 11/2009 | Phan et al. | |
| 2009/0275992 A1 | 11/2009 | Phan et al. | |
| 2009/0275993 A1 | 11/2009 | Phan et al. | |
| 2009/0275994 A1 | 11/2009 | Phan et al. | |
| 2009/0299412 A1 | 12/2009 | Marino | |
| 2009/0306671 A1 | 12/2009 | McCormack et al. | |
| 2009/0312763 A1 | 12/2009 | McCormack et al. | |
| 2009/0312798 A1 | 12/2009 | Varela | |
| 2009/0312800 A1 | 12/2009 | Chin et al. | |
| 2009/0318980 A1 | 12/2009 | Falahee | |
| 2010/0068003 A1 * | 3/2010 | Wagner | 411/386 |
| 2010/0076490 A1 | 3/2010 | Greenwald et al. | |
| 2010/0082065 A1 | 4/2010 | Butler et al. | |
| 2010/0087859 A1 | 4/2010 | Jackson, Jr. | |
| 2010/0094356 A1 | 4/2010 | Varela et al. | |
| 2010/0100135 A1 | 4/2010 | Phan | |
| 2010/0114175 A1 | 5/2010 | McKay | |
| 2011/0112436 A1 | 5/2011 | Jones et al. | |
| 2012/0010659 A1 | 1/2012 | Angert et al. | |
| 2012/0010662 A1 | 1/2012 | O'Neil et al. | |
| 2012/0010669 A1 | 1/2012 | O'Neil et al. | |
| 2012/0022603 A1 | 1/2012 | Kirschman | |
| 2012/0197311 A1 | 8/2012 | Kirschman | |

* cited by examiner

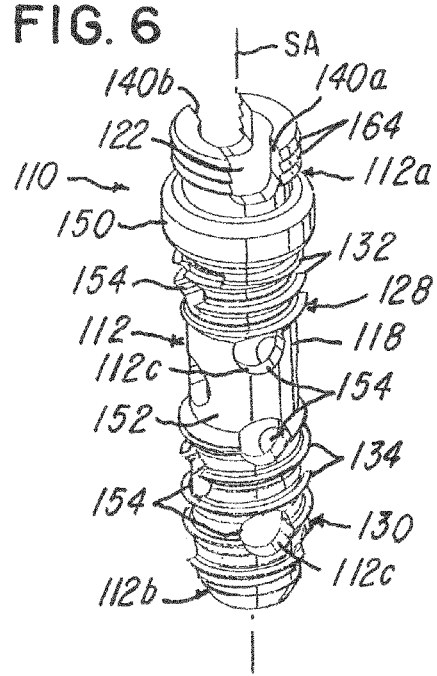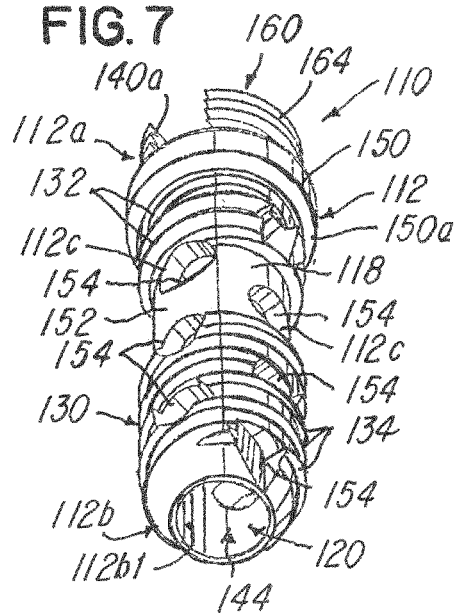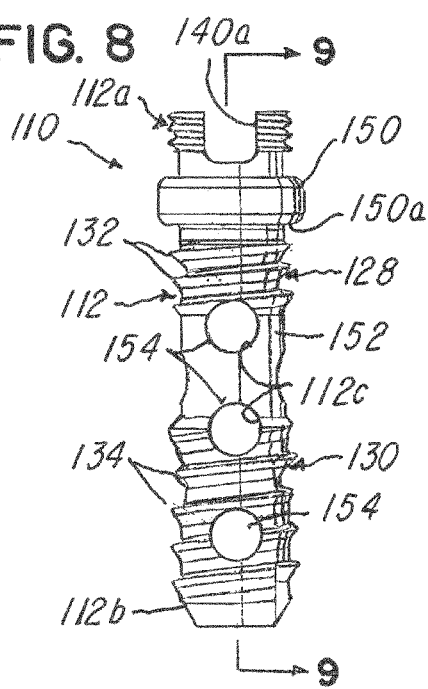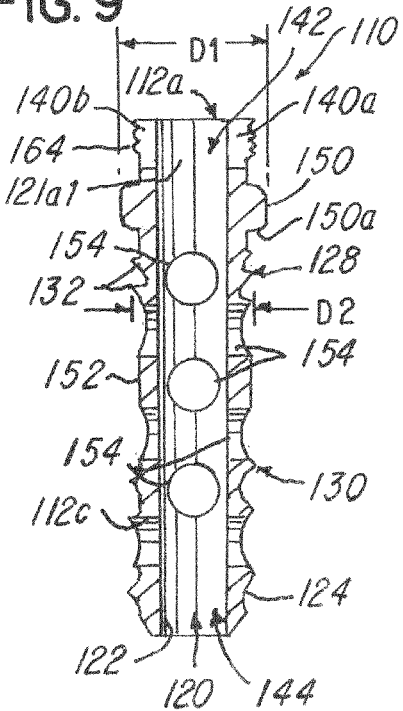

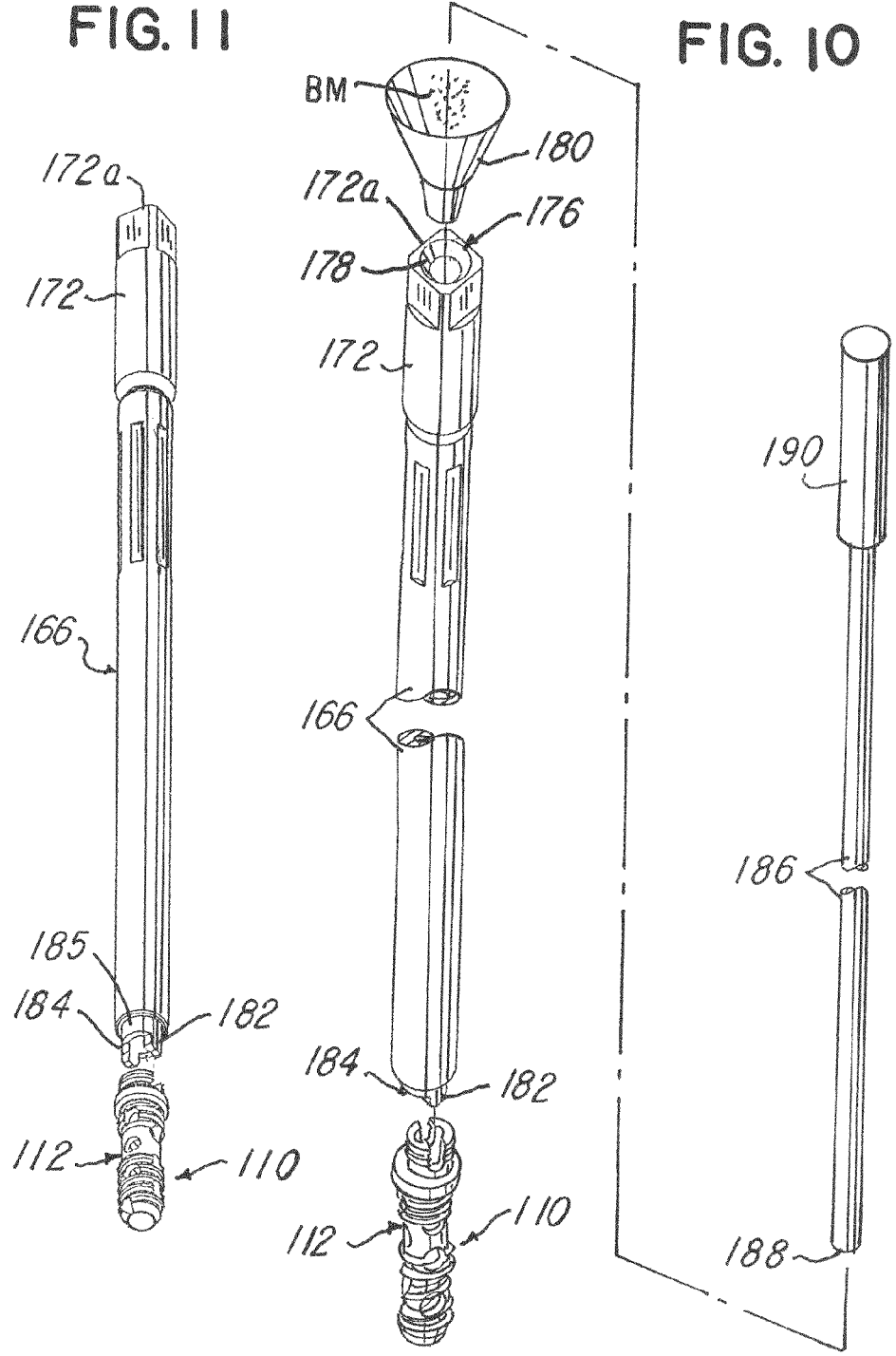

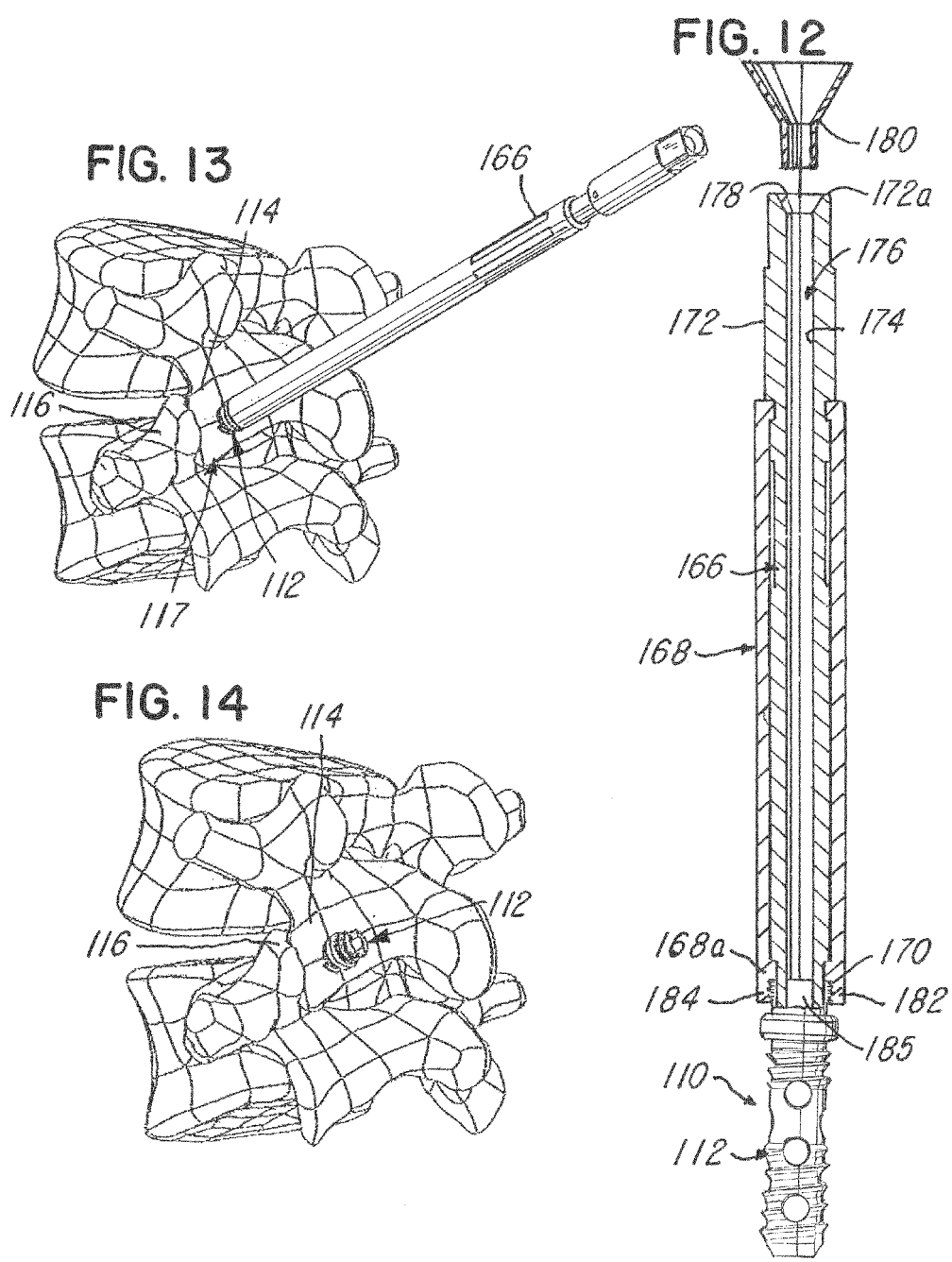

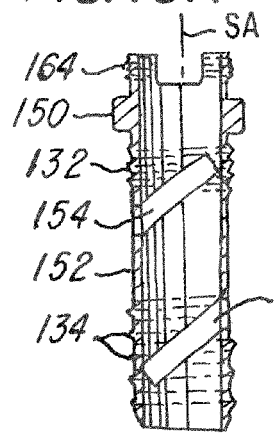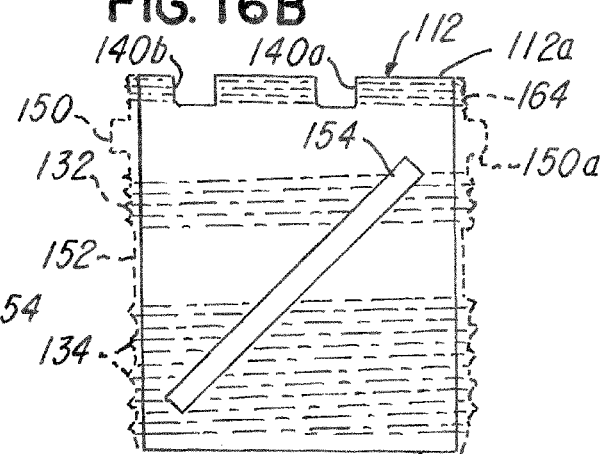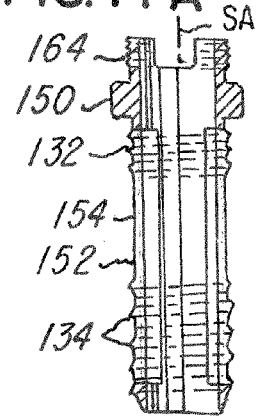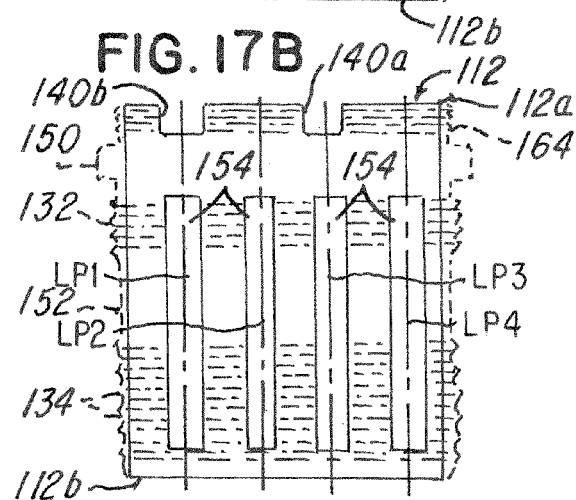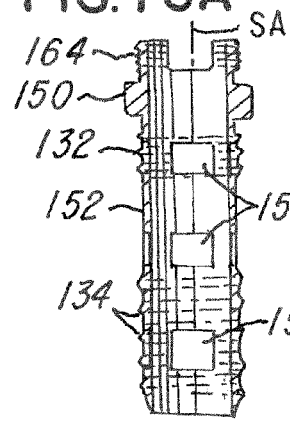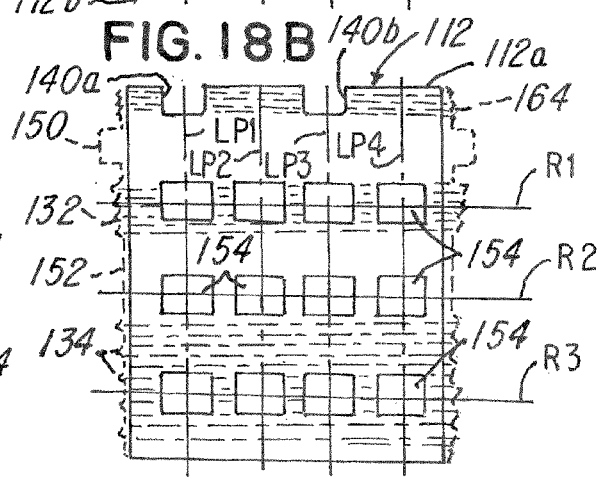

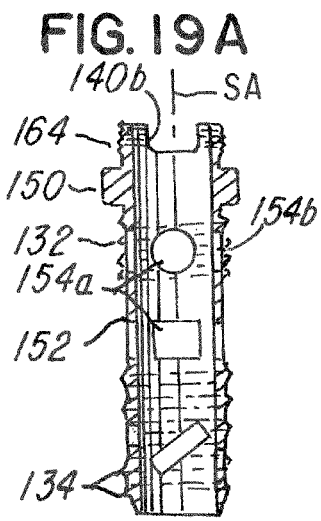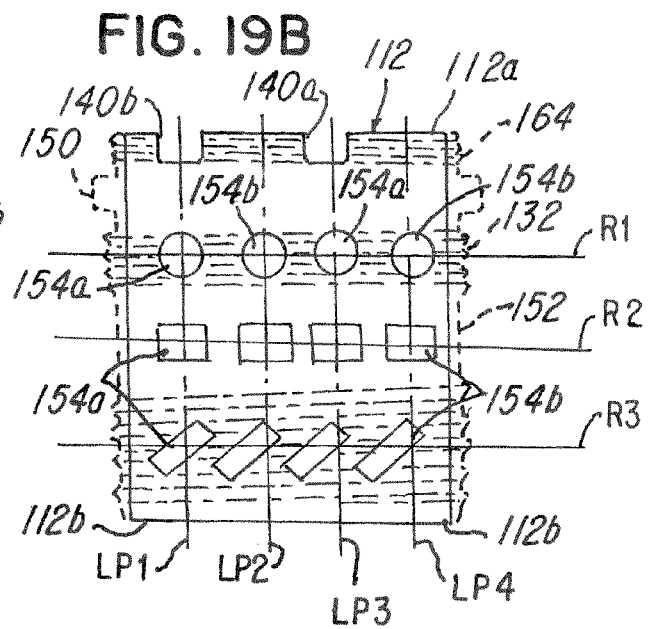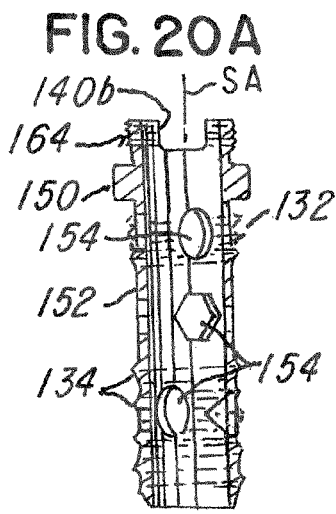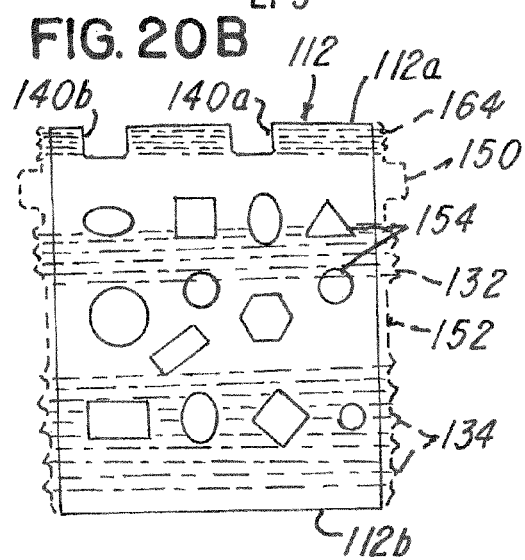

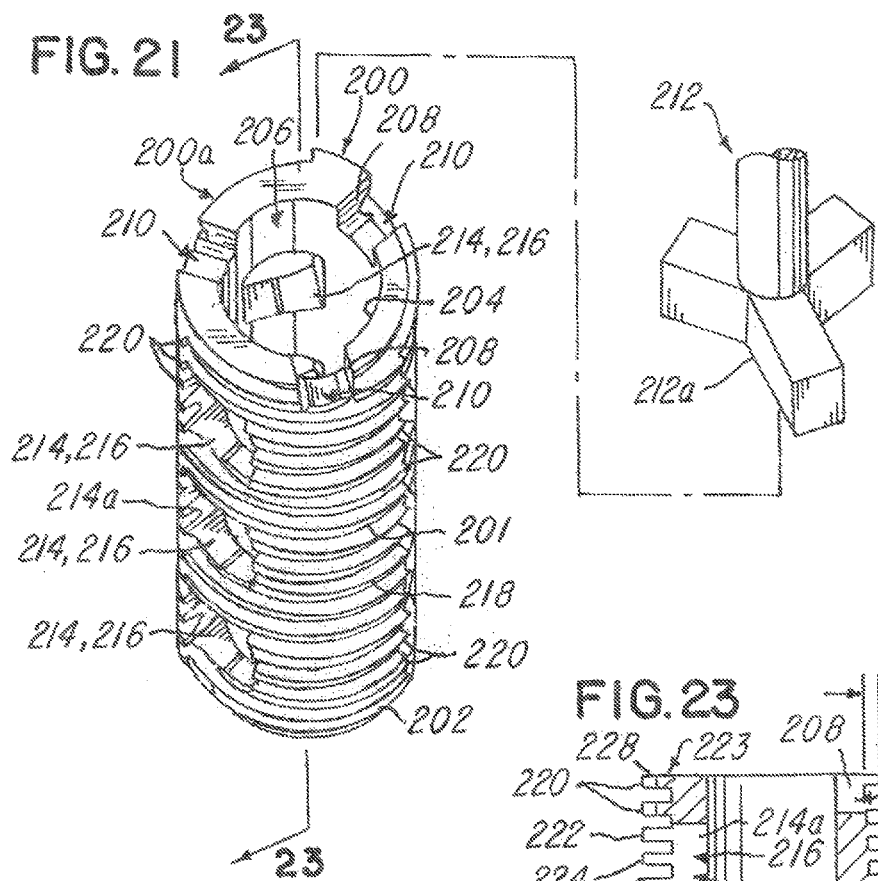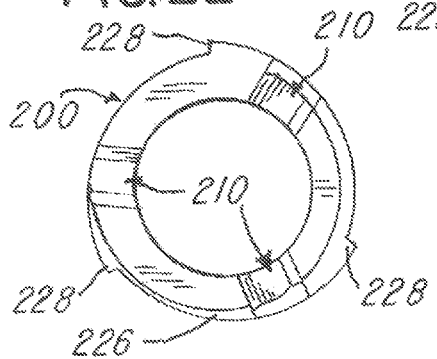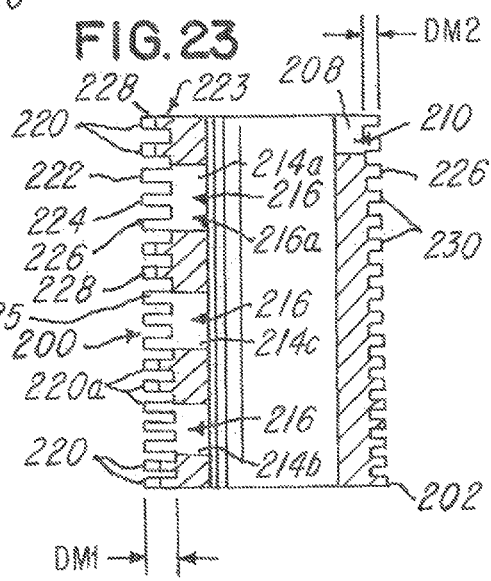

MINIMALLY INVASIVE SPINAL FACET COMPRESSION SCREW AND SYSTEM FOR BONE JOINT FUSION AND FIXATION

CROSS-REFERENCE TO RELATED APPLICATION

This application is a continuation-in-part of U.S. patent application Ser. No. 13/184,862 filed Jul. 18, 2011, which claims priority to U.S. Provisional Patent Application No. 61/365,906 filed Jul. 20, 2010, to which Applicant claims the benefit of the earlier filing dates and which applications are incorporated herein by reference in their entirety and made a part hereof.

BACKGROUND OF THE INVENTION

1. Field of the Invention

This invention relates to implants, and more particularly, to a spinal facet compression screw comprising a plurality of variable pitch thread zones and a buttress head. Another embodiment relates to a minimally invasive spinal facet joint fusion and fixation system.

2. Description of the Related Art

The field of spinal implantation burgeons with devices and methods for the achievement of fixation between adjacent vertebrae. The most common devices currently used for the fixation are pedicle screw systems. In a typical pedicle screw system, screws are placed in to the pedicles of adjacent vertebrae and are stabilized together using various separate rod or plate means. An emerging means for achieving fixation of adjacent vertebrae is the use of trans-facet fixation. Several devices listed below achieve fixation by placement of a screw or other means though the facet joint. This procedure has the advantage of being significantly less invasive than pedicle screw procedures, since it does not require a separate rod or plate means and only requires two bilateral screws to achieve fixation per level, rather than four in a pedicle screw system. For these reasons, trans-facet fixation has been growing in popularity.

A key goal of trans-facet fixation is the achievement of firm and direct contact of the opposing facet joint surfaces. Such contact is required for the desired bony fusion to take place. The current state of the art relies on the simple tightening of a lag screw to achieve external compression of the facet. This has limited effectiveness due to the limited ability of the relatively fragile facet joint to withstand external screw-tightening forces.

Variable pitch screws have been used in orthopedic surgery, particularly trauma repair, in the past. This is exemplified by the Herbert screw, invented in 1976. These screws, however, rely only on internal compression, and do not benefit from the external screw head buttressing as described in the current invention.

Some of the systems for bone fixation relating to facet fusion are shown or known from U.S. Patent Publications 20030208202 to Falahee; 20040087948 to Suddaby; 20040254575 to Obenchain et al.; 20050124993 to Chappuis; 20050149030 to Serhan; 20050267480 to Suddaby; 20060111779 to Petersen; 20060111780 to Petersen; 20060200149 to Hoy et al.; 20060212034 to Triplett et al.; 20060264953 to Falahee; 20070112428 to Lancial; 20070233092 to Falahee; 20070233093 to Falahee; 20080234758 to Fisher et al.; 20080255618 to Fisher et al.; 20080255619 to Schneiderman et al.; 20080255622 to Mickiewicz et al.; 20080255666 to Fisher et al.; 20080255667 to Horton; 20080262555 to Assell et al.; 20080275454 to Geibel; 20090036926 to Hestad; 20090036927 to Vestgaarden; 20090036986 to Lancial et al.; 20090054903 to Falahee et al.; 20090076551 to Petersen; 20090093851 to Osman; 20090099602 to Aflatoon; 20090105819 to Barry; 20090112264 to Lins; 20090125066 to Kraus et al.; 20090131986 to Lee et al.; 20090163920 to Hochschuler et al.; 20090177205 to McCormack; 20090187219 to Pachtman et al.; 20090192551 to Cianfrani et al.; 20090216273 to Cox; 20090234394 to Crook; 20090234397 to Petersen; 20090248082 to Crook et al.; 20090248089 to Jacofsky et al.; 20090264928 to Blain; 20090270929 to Suddaby; 20090275954 to Phan et al.; 20090275992 to Phan et al.; 20090275993 to Phan et al.; 20090275994 to Phan et al.; 20090299412 to Marino; 20090306671 to McCormack et al.; 20090312763 to McCormack et al.; 20090312798 to Varela; 20090312800 to Chin et al.; 20090318980 to Falahee; 20100076490 to Greenwald et al.; 20100082065 to Butler et al.; 20100087859 to Jackson; 20100094356 to Varela et al.; 20100100135 to Phan; 20100114175 to McKay;

Other systems are shown in U.S. Pat. No. 7,708,761 issued to Petersen; U.S. Pat. No. 7,699,878 issued to Pavlov et al; U.S. Pat. No. 7,608,094 issued to Falahee; U.S. Pat. No. 7,563,275 issued to Falahee et al.; U.S. Pat. No. 7,452,369 issued to Barry; U.S. Pat. No. 7,223,269 issued to Chappuis; U.S. Pat. No. 6,648,893 issued to Dudasik; U.S. Pat. No. 6,540,747 issued to Marino and U.S. Pat. No. 6,485,518 issued to Cornwall et al.

In order to perform a trans-facet fusion procedure, both a fixation element and a fusion element are required. The fixation element is typically a metallic screw and the fusion element is a bone graft material. This bone graft can be harvested from the patient at the time of surgery. Alternatively, donated-bone and synthetic bone substitute products may be used.

A disadvantage to prior art facet screw systems is that while they address the potential for percutaneous placement of the screw (fixation) component, none have provisions to incorporate the fusion component in this manner. Conversely, prior art bone graft systems have been developed which are wedged or inserted into the particular portion of the facet joint. Although these systems address the fusion component, they confer little, if any, mechanical fixation of the facet joint. With prior art systems, a biologic and screw component must be placed via a separate incisions and/or approaches. This defeats a major advantage of facet screw placement, i.e. a simple, minimally-invasive approach. This also limits the procedure to traditional operating room settings where larger procedures can be supported.

It should also be noted that fenestrated bone screws with an internal cavity are well-described in the prior art. Typically, such screw designs are intended for the injection of cement for the purpose of increasing screw stability. Such screws, however, are not designed to incorporate a fusion mass across two adjacent facet joints wherein the screw itself comprises both a fixation component and fusion component.

What is therefore needed is a fixation/fusion system wherein both the fixation and fusion component can be placed percutaneously and serially through the same small skin opening and via the same instrumentation.

Therefore, what is needed is a new device which draws together the opposing facet joint surfaces via internal compression in addition to external compression.

SUMMARY OF THE INVENTION

In one embodiment of the present invention, internal compression is achieved through the use of two thread zones of differing pitch. Upon placement of this screw, proximal threads are located in the upper facet half and distal threads are located in the lower facet half. Between these threads is a non-threaded screw shaft. By rotating the screw clockwise, rotation of the threads of differing pitches results in a relative movement of the lower facet half towards the upper facet half.

This results in the desired compression. Additionally, a screw head, located above the proximal threads serves to provide additional external buttressing to augment the internal compression.

A surgical implant used, in its preferred embodiment, for the support of spinal vertebrae. The implant comprises a screw element, which is placed through the facet joint of adjacent vertebra. The implant comprises a screw driver attachment zone, a non-threaded buttressing head with a wider diameter than the screw shaft, a proximal narrow-pitch thread, a non-threaded screw shaft, and a distal wide-pitch thread.

In an alternate embodiment, the proximal threads contain a bone-locking feature comprising linear slots in the thread, allowing for bone growth into the thread and helping to prevent the screw from loosening.

In another embodiment, the screw driver attachment zone has an additional set of threads to allow for the engagement of a screw driver locking sleeve. These threads have a handedness opposite of the proximal and distal threads to prevent disengagement of the screw driver locking sleeve.

One object of one embodiment is to provide an improved screw implant that utilizes internal and external compression.

Another object of another embodiment is to provide an improved implant for coupling and/or fusing facet bones of a facet joint.

Still another object of another embodiment is to provide an implant having a plurality of threads with differing thread pitches.

Yet another object of an embodiment is to provide a screw implant having a buttressing head against which a bone may be driven.

Yet another object of an embodiment is to provide a screw implant capable of driving a plurality of bones at different rates.

Another object of an embodiment is to provide a screw implant having locking features, such as a locking slot or aperture, for facilitating ingrowths of bone into the implant.

Another object of an embodiment is to provide an implant having threads associated with the screw head wherein the threads have a thread handedness that is opposite the thread handedness of the threads that engage bone.

Another object is to provide a thread that has anti-rotation locks, some of which may be in communication with a window or fenestration in the screw body.

Another object is to provide a screw body having a body having a lumen or bore where said body is fenestrated or has windows.

In one aspect, one embodiment comprises a surgical implant comprising a screw element having a screw head, a first thread having a first thread pitch, a second thread having a second thread pitch and an intermediate portion coupling the first and second thread pitches, the first and second thread pitches being different and the screw head defining a tool attachment zone, a buttressing head associated with the first thread and being dimensioned to be larger than a diameter of the first threads to provide external buttressing as the first and second threads compress a first bone and a second bone together.

In another aspect, another embodiment comprises a surgical implant comprising an elongated body having a first end and a second end, a screw head associated with the first end, a first thread having a first thread pitch associated with the first end, a second thread having a second thread pitch and an intermediate portion coupling the first and second thread pitches, the first and second thread pitches being different and the screw head defining a tool attachment zone, a buttressing head situated between the first thread and the screw head, the buttressing head being dimensioned to be larger than a diameter of the first threads to provide external buttressing to a first bone as the first and second threads compress a second bone against the first bone.

In still another aspect, another embodiment comprises a surgical screw implant comprising a generally cylindrical body defining a biological material receiving area, the generally cylindrical body having at least one screw thread zone having at least one thread, the generally cylindrical body comprising at least one aperture and the at least one aperture being in communication with the biological material receiving area and being adapted to receive biological material that can extrude through the at least one aperture to provided a fusion zone of the biological material and at least one bone in which a screw is screwed.

In still another aspect, another embodiment comprises a surgical implant system comprising a screw element for fixing a first bone and a second bone together, the screw element comprising a core having an inner wall that defines a hollow area and an outer wall having at least one threaded zone, the core being fenestrated with at least one window and the core being adapted to receive biological material for the promotion of osteosynthesis or fusing of the first bone and the second bone, and permitting the biological material to pass through the at least one window.

In yet another aspect, another embodiment comprises a screw for fixing and fusing a first bone and a second bone together, the screw comprising a wall defining an internal bore and a plurality of radially-spaced windows in communication with the internal bore.

In still another aspect, another embodiment comprises a method for fixing and fusing a first bone and a second bone together, comprising the steps of making an incision in a patient's skin, inserting a screw cage through the incision so that in traverses a joint or intersection between the first and second bone, using a tool for rotatably driving the screw into the first bone and the second bone to fix them together, inserting biological material into the tool before withdrawing the tool after the using step and driving the biological material through the tool and into the screw cage so that the biological material can engage the first and second bone or the joint or intersection so that the biological material can develop into a fusion mass across the joint or intersection, thereby fusing the first and second bones together.

In still another aspect, another embodiment comprises a surgical implant comprising a screw element having a screw head, a first thread having a first thread pitch, a second thread having a second thread pitch and an intermediate portion coupling the first and second thread pitches, the first and second thread pitches being different and the screw head defining a tool attachment zone, a buttressing head associated with the first thread and being dimensioned to be larger than a diameter of the first threads to provide external buttressing as the first and second threads compress a first bone and a second bone together.

In still another aspect, another embodiment comprises an introducer or inserter tool comprising a generally cylindrical body having a first end adapted to be secured to a screw element and a second end, the generally cylindrical body comprising an aperture or bore therethrough adapted to permit biological material to be passed there through and into the screw element.

These and other objects and advantages will be apparent from the following description, the accompanying drawings and the appended claims.

BRIEF DESCRIPTION OF THE DRAWINGS

FIG. 6 is a perspective view of another embodiment of the invention;

FIG. 7 is another perspective view of the embodiment shown in FIG. 6;

FIG. 8 is another view of the embodiment shown in FIG. 6;

FIG. 9 is a sectional view taken along the line 9-9 in FIG. 8;

FIG. 10 is a view showing the system with the screw element and the inserter tool and ramrod that may be used with it;

FIG. 11 is another view of the system shown in FIG. 10;

FIG. 12 is a sectional view illustrating the screw element mounted to the insertion tool and with portions of the insertion tool shown in section;

FIG. 13 is a view showing use of the system in order to screw the screw element into bone;

FIG. 14 illustrates the screw element after it has been screwed into bone;

FIG. 16A is a sectional view of a screw element having a single aperture that is situated in a spiral or helical;

FIG. 16 B is a developed view of the alternative embodiment screw element shown in FIG. 16A;

FIG. 17A is a sectional view of a screw element in accordance with another embodiment of the invention;

FIG. 17B is a developed plan view of the embodiment shown in FIG. 17A;

FIG. 18A is a sectional view of a screw element in accordance with still another embodiment;

FIG. 18B is a developed plan view of the embodiment shown in FIG. 18A;

FIG. 19A is a sectional view of still another embodiment of the invention;

FIG. 19B is a developed plan view of the embodiment shown in FIG. 19A;

FIG. 20A is a sectional view of a screw element in accordance with yet another embodiment of the invention;

FIG. 20B is a developed plan view of the embodiment shown in FIG. 20A, illustrating a random, staggered or uneven pattern of apertures or windows;

FIG. 21 is a view of another embodiment showing a continuous, constant pitch thread;

FIG. 22 is a plan view of the embodiment shown in FIG. 21; and

FIG. 23 is a second view taken along line 23-23 in FIG. 21.

DETAILED DESCRIPTION OF PREFERRED EMBODIMENTS

Figure 1:
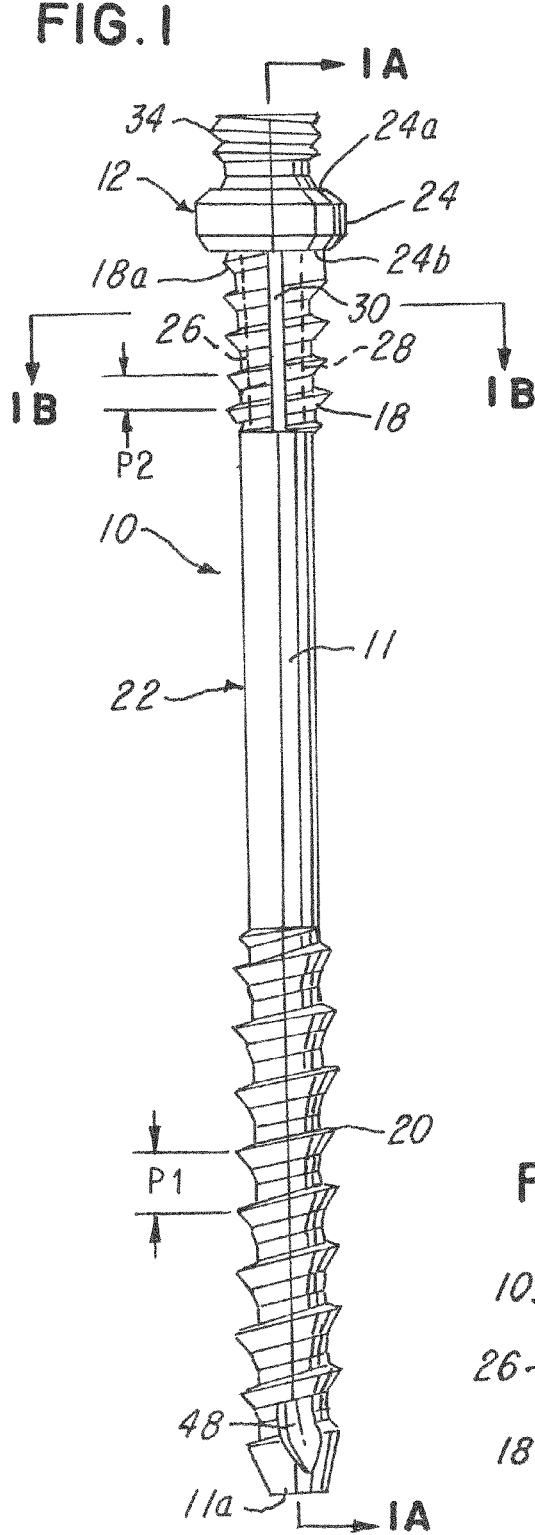
FIG. 1 is a view of an implant in accordance with one embodiment of the invention.
Figure 1A:
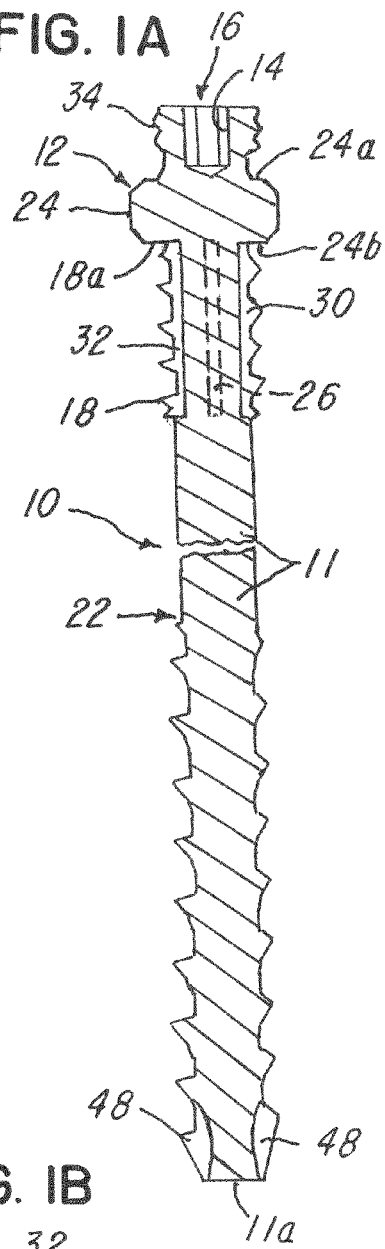
FIG. 1A is a sectional view taken along the line 1A-1A in FIG. 1.
Figure 2:
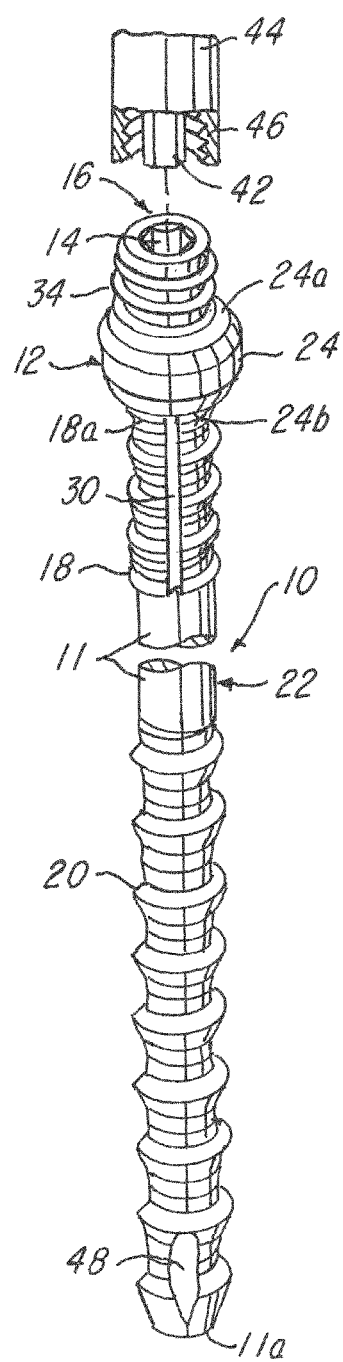
FIG. 2 is perspective view of the implant shown in FIG. 1.
Figure 3:
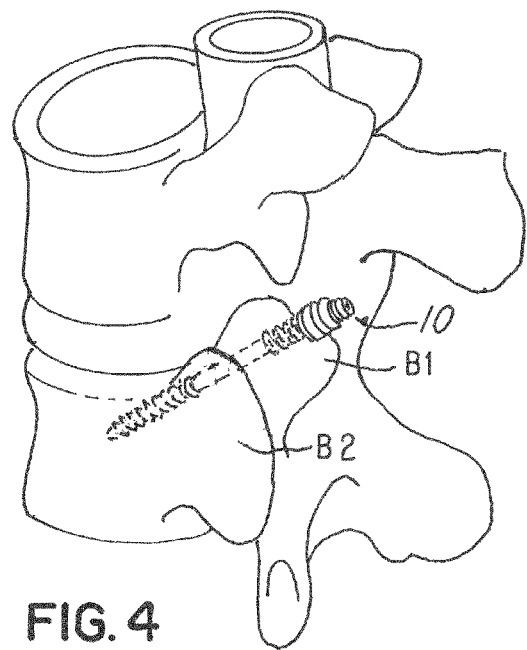
FIG. 3 is a view showing the implant screwed into a facet joint having a first or upper facet bone and a second or lower facet bone of a spinal column.
Figure 4:
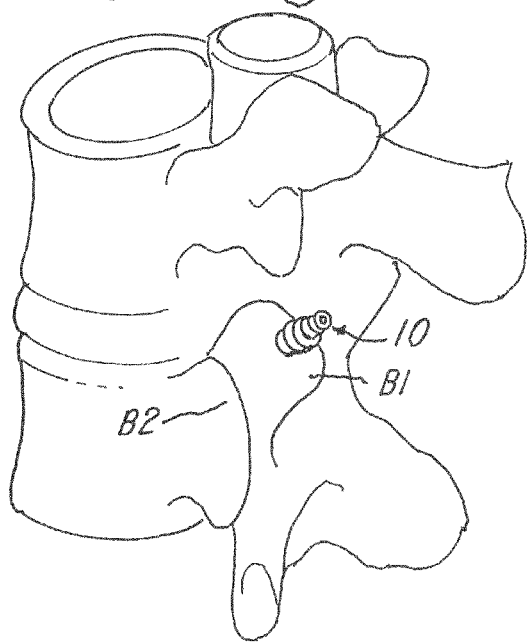
FIG. 4 is another view of the implant after it is screwed into the facet bones to lock the facet bones together.

Referring now to FIGS. 1-5D, a surgical implant 10 is shown. In the embodiment being described, the surgical implant 10 comprises a body 11. The body 11 comprises a screw head 12 having an aperture or tool attachment zone 16. In the illustration, the tool attachment zone 16 comprises an internal wall 14 that defines the aperture or tool attachment zone 16 (FIG. 1A) in the form of a tool receiving aperture for receiving a screw driver 40 (FIG. 2).

The surgical implant 10 further comprises a proximal or first thread 18, a distal or second thread 20 and an intermediate portion 22 that is not threaded and that is integral or monolithically formed with the first thread 18 and second thread 20 as shown. In the illustration being described, it should be understood that pitch distances of each of the first threads 18 and second threads 20 are different. Thus, note in FIG. 1 that a pitch distance P1 for the distal or second threads 20 is larger than a pitch distance P2 of the proximal or first thread 18. Advantageously, the rotation of the first and second threads 18 and 20 results in a relative movement of a first bone B1, such as a lower facet bone (FIGS. 5A-5D), relative to a second bone B2, such as an upper facet bone. This results in a desired compression of the first bone B1 against the second bone B2 as described later herein relative to FIGS. 5A-5D.

As further illustrated in FIGS. 1, 1A and 2, the body 11 of surgical implant 10 further comprises a buttressing head 24. In the illustration being described, the buttressing head 24 is integrally or monolithically formed in the screw body 11 as shown. Note that the buttressing head 24 is generally cylindrical and has a first surface or side 24a and a second surface or side 24b that are generally planar. In the illustration being described, the second surface or side 24b is adjacent to an end 18a of the first or proximal thread 18 and is associated therewith. The buttressing head 24 is larger in diameter than both the first and second threads 18 and 20, and provides a buttress or stop that facilitates providing external buttressing as the first and second threads 18 and 20 compress the first bone B1 and the second bone B2 together. In other words, as the first thread 18 drives the second bone B2 leftward (as viewed in FIGS. 5A-5D) upon rotation of the body 11, the second bone B2 ultimately engages the second side 24b and the first bone B1 is driven by the second or distal thread 20 toward the second bone B2 until they engage and are in compression. Thus, the first and second threads 18 and 20 provide an internal compression of the first and second bones B1 and B2, and the surface 24b of buttressing head 24 provides a surface 24b against which the first bone B1 can drive and compress the second bone B2, thereby providing an external compression.

As mentioned earlier, the pitch distance P1 (FIGS. 1 and 1A) of the second or distal threads 20 is larger than the pitch distance P2 of the first or proximal thread 18 which means that the first and second threads 18 and 20 drive their respective bones B2 and B1 (as viewed in FIG. 5A-5D) at different leads or rates. In this regard, the rate of driven movement of the first bone B1 is greater than the rate of the driven movement of the second bone B2, as illustrated in FIGS. 5A-5D.

Note that the intermediate portion 22 of the body 11 is not threaded and has a diameter smaller than the diameter of the first and second threads 18 and 20 and the buttressing head 24. This further facilitates driving the first and second bones B1 and B2 together.

Figure 1B:
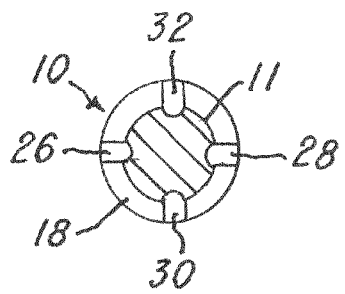
FIG. 1B is a sectional view taken along the line 1B-1B in FIG. 1.

In the illustration being described, the surgical implant 10 further comprises a plurality of locking slots or apertures 26, 28, 30 and 32 (FIG. 1B) that are generally elongated slots or apertures located in the first threads 18. Although not shown, the second threads 20 could also comprise one or more locking slots or apertures. In the illustration being described, the locking slots or apertures 26-32 are elongated and generally parallel to an axis of the body 11, as best illustrated in FIG. 1A. In the embodiment being described, the body 11 comprises locking slots or apertures 26, 28, 30 and 32, that are radially spaced about an axis A (FIG. 1A) of the body 11, as best illustrated in FIG. 1B. In the illustration being described, the locking slots or apertures 26-32 are generally elongated and linear, but it should be understood that they could comprise another configuration, such as a spiral or helical configuration or shape.

In the illustration being described, the locking slots or apertures 26-32 facilitate allowing for bone growth over and/or into the body 11 of the surgical implant 10 after the surgical implant 10 is screwed into a patient. The locking slots or apertures 26-32 facilitate preventing the surgical implant 10 from loosening after the surgical implant 10 is screwed into the patient by providing areas for such bone growth. In the illustration being described, the embodiment is shown as having four locking slots or apertures 26-32, but it should be appreciated that more or fewer locking slots or apertures 26-32 could be provided in at least one of both a plurality of the first threads 18, the second threads 20 and/or in the intermediate portion 22. In the illustration being described, the locking slots or apertures 26-32 are located in the first thread 18.

As is conventionally known, the second threads 20 may have a plurality of notched out areas 48 (FIGS. 1-1A) to facilitate the start of the surgical implant 10 into the first and second bones B1 and B2.

In another embodiment, the screw head 12 comprises a third thread 34 (FIGS. 1, 1A and 2) at the tool attachment zone 16 to allow for engagement of and connection to a surrounding or tool locking sleeve 44 (FIG. 2). In the illustration being described, the handedness of the third thread 34 is opposite the handedness of each of the first and second threads 18 and 20. For example, if the first and second threads 18 and 20 are right-handed threads, then the third thread 34 is left-handed, and vice versa, if the first and second threads 18 and 20 are left-handed, then the third thread 34 are right-handed. The opposite handedness facilitates preventing disengagement of the surgical implant 10 from the screw driver 40. Note in FIG. 2 that the screw driver 40 comprises a male screw driver tool 42 that is received in the mating female opening in the tool attachment zone 16 and a surrounding sleeve 44 having threads 46 that mate with the third thread 34. In the illustration being described, the opposite handedness of the first and second threads 18 and 20 from that of the third threads 34 facilitates preventing disengagement of the screw driver 40 from the male screw driver tool 42. It should be understood that the sleeve 44 remains stationary during rotation of the screw driver tool 42.

Note that the first or proximal threads 18 have pitch distance P2 that is less than pitch distance P1 than the second or distal threads 20. This feature causes the bone B1 that receives the second or distal thread 20, such as a facet joint surface, to move at a rate R1 toward the buttressing head 24. The opposing bone surface B1*a* (FIGS. 5A and 5D) that receives the first or proximal thread 18 moves at a rate R2 that is slower than the rate R1. Stated another way, the second or distal thread 20 and the first or proximal thread 18 move opposing bone surfaces B1*a* and B2*b*, respectively, toward the buttressing head 24 at the first and second rates R1 and R2 until the second bone surface B2*a*, such as an opposing facet joint surface, comes into contact with the surface 24*b* of the buttressing head 24. As mentioned earlier, by rotating the screw clockwise in the example, rotation of the first and second threads 18 and 20 of the differing pitches results in a relative movement of the lower bone, such as a lower facet half toward an upper bone, such as the upper facet half, until the upper facet half is situated and compressed between the buttressing head 24 and the lower facet half thereby resulting in a desired compression. Again, note that the external buttressing head 24 buttresses the compression.

Figure 5A:
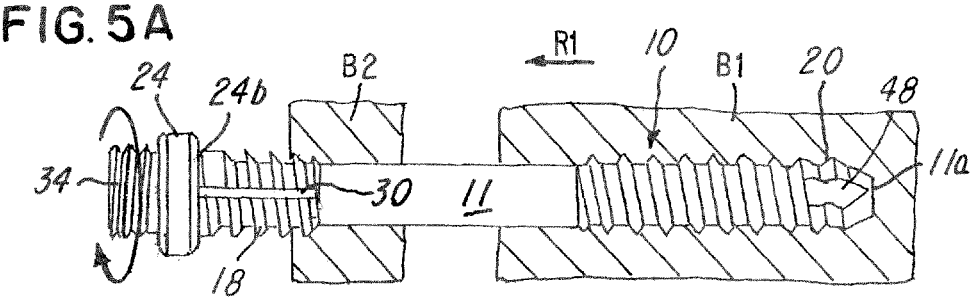
FIGS. 5A-5D illustrate the relative movement of the first bone relative to a second bone during rotation of the implant.
Figure 5B:
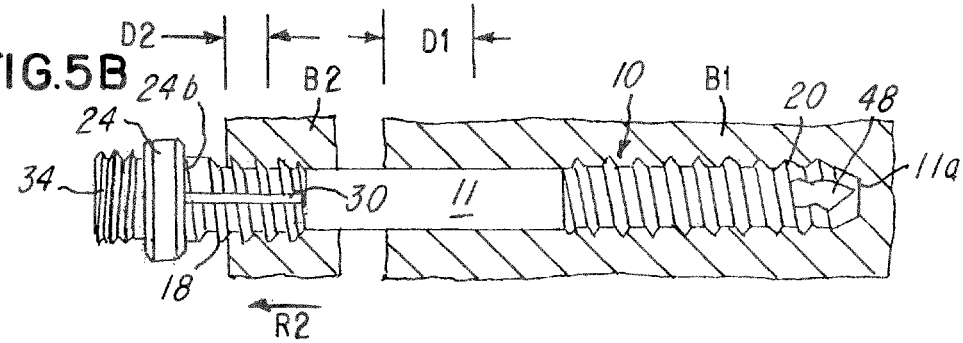
Figure 5C:
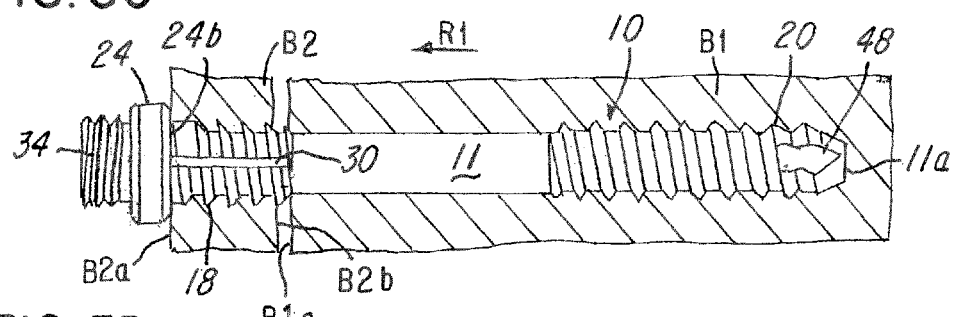
Figure 5D:
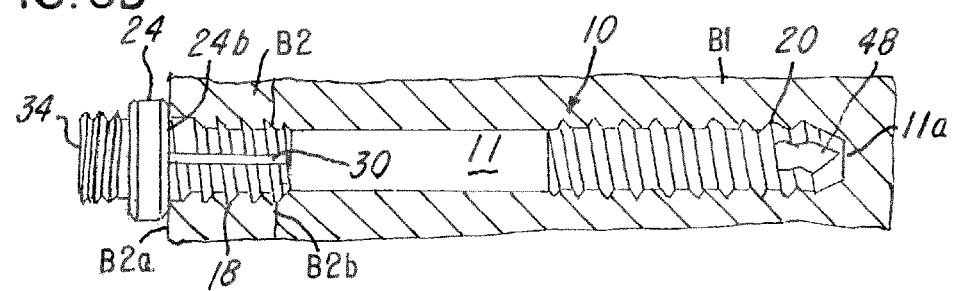

As shown in FIGS. 5A-5D, the distal end 11*a* (FIG. 1) of surgical implant 10 is screwed into the first bone B1 and the proximal thread is screwed into the second bone B2. When the surgical implant 10 is rotated clockwise, the distal thread 20 is screwed into the bone B1 and drives it leftward (as viewed in FIGS. 5A-5C) a distance D1 as shown in FIGS. 5A and 5B. Substantially simultaneously, the first or proximal threads 18 are screwed into the bone B2 and drive it relative to the buttressing head 24 leftward (as viewed in FIGS. 5A-5C) a distance D2 as shown in the comparison of FIGS. 5A, 5B and 5C. This relative movement of the bones B1 and B2 continues as illustrated in FIGS. 5C and 5D during rotation of the body 11 of surgical implant 10 until a surface B2*a* of the bone B2 engages the buttressing head 24 and the surface B1*a* of bone B1 engages the generally opposing surface B2*b* as illustrated in FIGS. 5C and 5D. In this regard, notice that the bone surface B1*a* engages the bone surface B2*b* and drives it toward the buttressing head 24, thereby compressing the bones B1 and B2 together and compressing the bone B2 against the buttressing head 24. The external compression and internal compression facilitate securing the bones B1 and B2 together.

Advantageously, the system, method and implant described herein provide a means for fusing bones, especially the facet bones of a facet joint. The surgical implant 10 provides additional buttressing and compression of at least one or both of the bones that are fused or secured together.

Referring now to FIGS. 6-20B, another embodiment of a surgical screw implant system 110 is shown. In this embodiment, a surgical screw implant system 110 comprises a screw element 112 for fixing a first bone 114 (FIGS. 13 and 14) and a second bone 116 together. As with the first embodiment, the surgical screw implant system 110 is particularly adapted for use with facet bones and fusion of a facet joint, but could be used with other joints as well. In the illustration being described, the screw element 112 comprises a generally cylindrical body or core 118 defining a biological material receiving area, hollow area or bore 120 (FIG. 7). The generally cylindrical body or core 118 is circular in the example and comprises an inner surface wall 122 and an outer surface or wall 124. Note that the inner surface wall 122 defines the biological material receiving area, hollow area or bore 120.

The outer surface or wall 124 comprises at least one or a plurality of screw thread zones 128 and 130 that define first and second screw threads 132 and 134, respectively. Although the embodiment being described herein illustrates a plurality of screw thread zones 128 and 130, it should be appreciated that the outer surface or wall 124 could have a single screw thread traversing a portion or the entire length of the outer surface or wall 124 or it could have other threads as well. As mentioned later, the first and second screw threads 132 and 134 have different thread pitches, but they could be the same. An embodiment shown in FIGS. 21 and 22 illustrate a single thread traversing an entire length of the screw. This embodiment will be described later herein.

Note in the illustration being described, that the biological material receiving area, hollow area or bore 120 extends through an entire length of the screw element 112 in the illustration being described. In this regard, note that the screw element 112 comprises a tool-receiving end 112a (FIG. 8) and an end or screw tip 112b as shown. Note that the tool-receiving end 112a comprises a generally U-shaped channel 136 (FIG. 8) defined by a first generally U-shaped wall 140a and a second U-shaped wall 140b (FIG. 6). The tool-receiving end 112a comprises an inner wall 112a1 (FIG. 9) that defines an opening or aperture 142 and is in communication with the biological material receiving area, hollow area or bore 120 as shown. Likewise, the end or screw tip 112b (FIG. 7) comprises an inner wall 112b1 that defines an opening or aperture 144 (FIG. 7) that also opens into the biological material receiving area, hollow area or bore 120. It should be understood that while the screw element 112 has been shown having the inner wall 112b1 that defines the opening or aperture 144, it should be understood that the screw could be closed at this end. In the illustration being described, however, the opening or aperture 144 and the biological material receiving area, hollow area or bore 120 defines a lumen in the generally cylindrical body or core 118.

Referring back to FIGS. 6-9, it should be understood that the first and second screw threads 132 and 134 in the at least one or plurality of screw thread zones 128, 130, respectively, could have the same pitch and/or one of them could extend along an entire length of the outer surface or wall 124. Alternatively, the first and second screw threads 132 and 134 could have different pitches similar to the embodiment described earlier herein relative to FIGS. 1-5D. Note also that, like the embodiment described earlier herein relative to FIGS. 1-5D, the first screw thread 132 could comprise a thread pitch that is smaller than a thread pitch of the second screw thread 134 as shown. Like the embodiment described earlier herein relative to FIGS. 1-5D, the first thread pitch and the second thread pitch are different so that the first screw thread 132 may threadably engage and drive the first bone 114 to be fused at a first rate and the second screw thread 134 may threadably engage and drive the second bone 116 to be fused toward the first bone 114 at a second rate, wherein the second rate is greater than the first rate. In the illustration being described and as shown in FIGS. 6-9, note that the first screw threads 132 are proximal threads and the second screw threads 134 are distal threads, with the first and second screw threads 132, 134 driving the first and second bones 114 and 116, respectively, toward a buttressing head 150 which is similar in design and function as the buttressing head 24 described earlier herein relative to the embodiment in FIGS. 1-5D.

The buttressing head 150 comprises an engaging surface 150a (FIG. 9) against which the first bone 114 engages when the surgical screw implant system 110 is screwed into bone. As with the earlier embodiment, note that the buttressing head 150 comprises a diameter D1 that is slightly larger than the diameter D2 of the largest of the first or second screw threads 132 and 134 so that the engaging surface 150a extends past the first screw threads 132 as shown. This enables the engaging surface 150a to provide an external platen or external buttress engaging surface 150a against which the first bone 114 may be driven when the surgical screw implant system 110 is screwed into bone. Thus, the engaging surface 150a provides an external buttress against which the first bone 114 may be driven.

In the illustration being described and like the embodiment described earlier herein relative to FIGS. 1-5D, note that the screw element 112 comprises a smooth intermediate area or portion 152 that couples the first and second screw threads 132 and 134 as shown. The intermediate area or portion 152 is generally smooth and not threaded to facilitate the second bone 116 (FIG. 13) being driven into engagement with the first bone 114 similar to the first embodiment and as illustrated in FIGS. 5A-5D.

Referring now to FIG. 9, note that the biological material receiving area, hollow area or bore 120 extends through an entire longitudinal length of the generally cylindrical body or core 118 and defines the lumen therein for receiving osteo-biological or biological material BM (FIG. 10). The types of materials that can be inserted are bone graft from the patient (autograft), bone graft from a cadaver (allograft), bone components, or synthetic materials which can cause adjacent bone to grow (osteoinductive materials), or allow adjacent bone to grow into the material (osteoconductive materials). Other examples include various phosphate, carbonate or silicate compounds. Lastly, engineered peptides, such as bone morphogenic protein (BMP) can be used. Again, the biological material receiving area, hollow area or bore 120 is elongated and is coaxial with a longitudinal screw axis SA (FIG. 6) of the screw element 112. As alluded to earlier herein, the end or screw tip 112b is open by the opening or aperture 144, but it could be closed so that the biological material receiving area, hollow area or bore 120 would only extend partially through the screw element 112.

A significant feature of the embodiment being described is that the screw element 112 is adapted to receive biological material BM for the promotion of osteosynthesis or fusing of the first bone 114 to the second bone 116 while substantially simultaneously mechanically fixing the first and second bones 114 and 116 together with the first and second screw threads 132 and 134, respectively. To facilitate the fusing, the generally cylindrical body or core 118 is fenestrated and comprises at least one or a plurality of windows or apertures 154 as shown. For ease of illustration, the embodiment will be described showing a plurality of windows, but it should be understood and as mentioned that a single window or aperture could be provided in the generally cylindrical body or core 118. For example, a single continuous window, such as a rectangular elongated window, helical or spiral window or other aperture in the generally cylindrical body or core 118 could be provided. Various illustrations of the plurality of windows are shown and described later herein relative to FIGS. 16A-20B.

In the illustration being described, the generally cylindrical body or core 118 comprises the plurality of windows or apertures 154 as mentioned. The plurality of windows or apertures 154 are defined by a plurality of internal walls 112c as illustrated in FIGS. 8 and 9. In the illustration being described, the at least one or plurality of windows or apertures 154 permit the biological material BM (FIG. 11) to pass through, extrude or extend radially from the biological material receiving area, hollow area or bore 120 and through the plurality of windows or apertures 154 and the opening or aperture 144 at the screw tip 112b to adjacent surrounding bone. Thus, it should be appreciated that after the screw element 112 is screwed into the first and second bones 114 and 116 and the first and second bones 114 and 116 are fixed together, biological material BM may pass from the biological material receiving area, hollow area or bore 120 and through the plurality of windows or apertures 154 and into engagement with the first and second bones 114 and 116 to permit the biological material BM to engage and fuse the first and second bones 114 and 116 and a joint 117 (FIG. 13) between them.

Advantageously, the biological material receiving area, hollow area or bore 120 is adapted to receive the biological material BM and to provide a fusion mass transferring across or even into a joint, such as a facet joint 117 (FIG. 13), and infusion with each of the first and second bones 114 and 116. It should be appreciated, therefore, that the surgical screw implant system 110 provides or is adapted to fix a plurality of bones, such as the first bone 114 and the second bone 116, and substantially simultaneously, to fuse the plurality of bones together and provide a fusion mass between them or across the joint 117.

Returning to FIGS. 6-9, note that the plurality of windows or apertures 154 are spaced about the screw axis SA as illustrated. In the illustration being described, the plurality of windows or apertures 154 are similar shapes and circular and spaced longitudinally and radially as illustrated in FIGS. 6 and 9. Although the illustration shown shows that the plurality of windows or apertures 154 are spaced substantially evenly, longitudinally or circumferentially, it should be understood that they could be different shapes and spaced or staggered in another orientation, such as in an uneven orientation or a staggered orientation as illustrated in FIGS. 20A-20B.

Figure 15:
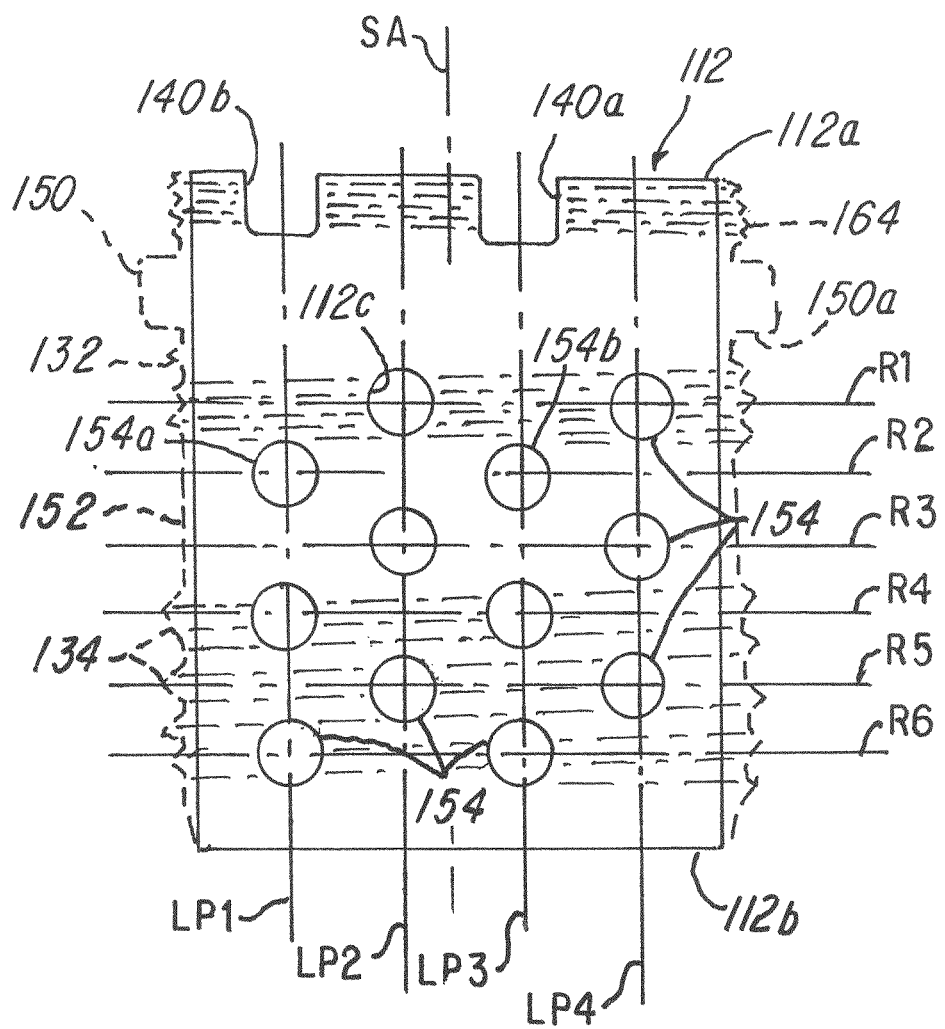
FIG. 15 is a developed view showing a generally cylindrical body of the screw element laid out in planar form to illustrate the plurality of apertures used to permit biological material to extrude or pass from inside the screw element to outside the screw element.

FIG. 15 illustrates a developed or planar view of the screw element 112 shown in FIGS. 6-9 and the layout or position of the plurality of windows or apertures 154 in the generally cylindrical body or core 118. Note that the plurality of windows or apertures 154 comprise a plurality of apertures that lie in radial or horizontal planes, such as a first radial plane R1, a second radial plane R2, a third radial plane R3, a fourth radial plane R4, a fifth radial plane R5 and a sixth radial plane R6 and so on. Likewise, the plurality of windows or apertures 154 comprise some apertures 154 that lie in a first longitudinal plane LP1, a second longitudinal plane LP2, a third longitudinal plane LP3 and a fourth longitudinal plane LP4. Note that the plurality of windows or apertures 154 that lie in the longitudinal planes LP1, LP2, LP3 and LP4 are spaced longitudinally and generally parallel to the screw axis SA as shown. The apertures 154 lying in the longitudinal planes LP1 and LP3 also lie in a common or radial plane, so that, for example, the window or aperture 154a in longitudinal plane LP1 is situated along the same radial plane R2 as the window or aperture 154b as shown. Likewise, some of the plurality of windows or apertures 154 that lie in the longitudinal planes LP2 and LP4 are spaced and lie in substantially the same or common radial planes as illustrated. In contrast, note that the plurality of windows or apertures 154 in the longitudinal planes LP1 and LP3 are staggered or offset relative to the plurality of windows or apertures 154 in the longitudinal planes LP2 and LP4. Likewise, the apertures 154 that lie in the radial planes R1, R3 and R5 are offset or staggered relative to the plurality of windows or apertures 154 that lie in the radial planes R2 and R4 and R6. The staggered or offset configuration of the plurality of windows or apertures 154 facilitate biological material BM being passed through, expanded or extruded from the biological material receiving area, hollow area or bore 120 in multiple and different radial directions and into adjacent bone, which further facilitates fusion.

In the illustration being described, two or three apertures 154 lie in each radial plane R1-R6 and each longitudinal plain LP1-LP4, but more or fewer apertures could be provided. The apertures are shown as having a common size, but they could have different sizes or shapes as illustrated in FIGS. 17A-20B. As mentioned earlier, a single aperture could be used having a shape that facilitates extrusion.

In the illustration being described, the plurality of apertures 154 that are defined by the plurality of interior walls 112c, respectively, are generally circular, elliptical, rectangular, hexagonal, polygonal or other desired shapes. For example, at least one or a plurality of apertures 154 could be an elongated (as shown in FIGS. 16A-17B) or continuous wall that extends along the longitudinal axis or spiral or helix about the axis if desired. FIGS. 16A-20B illustrate other exemplary shapes, sizes and patterns of apertures 154. FIGS. 16A-16B illustrate a generally rectangular aperture 154 that defines a spiral or helical aperture about the screw axis SA of the screw element 112. FIGS. 17A-17B illustrate a plurality of elongated apertures that having axes that are generally parallel to the screw axis SA. FIGS. 18A-18B illustrate still another example aperture 154 size and pattern wherein a plurality of square or even rectangular apertures are situated such that their axes lie in planes that are generally perpendicular to the screw axis SA. FIGS. 19A-19B illustrate still another example of the plurality of apertures 154 having different shapes. FIGS. 20A-20B illustrate a plurality of apertures having different shapes and that are situated, for example, in a random or staggered pattern.

Thus, it should be understood that the generally cylindrical body or core 118 could have the plurality of windows or apertures 154 that are staggered, spaced unevenly, of different shapes or sizes, spaced longitudinally or spaced circumferentially about the axis SA of the core.

As illustrated in FIGS. 6, 9 and 15-20B, at least one or a plurality of the plurality of windows or apertures 154 extend through at least one or both of the first screw threads 132 and second screw threads 134 as illustrated. Also, at least one or a plurality of windows or apertures 154 may extend through the intermediate portion 152 of the generally cylindrical body or core 118 as shown. In one embodiment, it is desirable to maximize the open area defined by the plurality of windows or apertures 154, so long as the implant is not mechanically weakened.

A significant advantage of the embodiment being described is that the biological material BM may be provided in the biological material receiving area, hollow area or bore 120 and extruded or passed through at least one or a plurality of windows or apertures 154, and the opening or aperture 144 so that the biological material BM may engage and fuse with bones situated outside the at least one or a plurality of windows or apertures 154 and opening or aperture 144, thereby facilitating fusing of at least or one or a plurality of the first and second bones 114 and 116 with the biological mass inside the biological material receiving area, hollow area or bore 120. As mentioned earlier herein, the screw element 112 may facilitate and provide a system or means for injecting the biological material BM and forcing it against and into engagement with the first and second bones 114 and 116, and also provide a system or means for injecting the biological material BM into a joint 117 between the first and second bones 114 and 116, which also facilitates fusing of the first and second bones 114 and 116. It should be understood that each of the plurality of windows or apertures 154 are adapted and sized to permit the biological material BM being used to be extruded generally laterally or radially from the screw element 112 so that the biological material BM may come into contact and fuse with any bone situated outside the plurality of windows or apertures 154.

Returning to the illustration shown in FIGS. 6-9, again note that at least some of the plurality of windows or apertures 154 extend or traverse through at least one or both of the first and second screw threads 132 and 134. In the illustration being shown in FIGS. 6 and 15, note that the plurality of threads and longitudinal planes LP2 and LP4 that lie in the radial plane R1 traverse or pass through the first screw thread 132. Likewise, the plurality of windows or apertures 154 that lie in the longitudinal planes LP1 and LP3 also lie in the radial plane R6 pass through the second screw threads 134 as shown. Note that the plurality of apertures 154 that lie in the longitudinal planes LP2 and LP4 and in the radial plane R3 traverse only through the intermediate portion 152. Again, the staggered and longitudinal and radial arrangement of the plurality of windows or apertures 154 facilitates fusion because it illustrates one maximization of the window area.

The generally cylindrical body or core 118 has been shown as being generally circular in cross-section, but it could comprise other shapes as well, so long as it can be threaded and screwed into bone.

At the tool-receiving end 112a of the generally cylindrical body or core 118, is the tool attachment zone 160 (FIG. 7) at the tool-receiving end 112a. The tool attachment zone 160 comprises a plurality of threads 164 in the tool-receiving end 112a. In the illustrating being described, the plurality of threads 164 allow for engagement and locking of an introducer or inserter tool 166 (FIGS. 12 and 13) to the screw element 112. The introducer or inserter tool 166 is adapted to be both a screw element 112 driver and a device or means for placement or insertion of biological material BM into the lumen or biological material receiving area, hollow area or bore 120 of the screw element 112.

In the illustration being described, the introducer or inserter tool 166 comprises a sleeve 168 that has an end 168a that comprises a plurality of threads 170 as illustrated in FIG. 12. The threads 164 have a handedness that is opposite the handedness of the first and second screw threads 132 and 134 and similar to the embodiment described earlier herein relative to FIGS. 1-5D. Likewise the mating threads 170 of the sleeve 168 of the tool 166 also have a handedness that mate with the threads 164. In the embodiment being described, the handedness is left-handedness so that when the tool is removed from the screw element 112, it is rotated in a direction that is common with a direction of rotation when the screw element 112 is being screwed into the first and second bones 114 and 116.

Note that the introducer or inserter tool 166 has an interior guide sleeve 172 having an inner wall 174 that defines an aperture or internal bore 176 for receiving biological material BM and/or other tools (not shown). In the illustration being described, the guide sleeve 172 comprises an end 172a having a beveled surface 178 that facilitates guiding and introducing the biological material BM or tools into the aperture or internal bore 176. In this regard, note that the surgical screw implant system 110 may comprise, for example, a funnel 180 for receiving the biological material BM and guiding it into the aperture or internal bore 176.

The guide sleeve 172 comprises a plurality of forks, aligning guides, coupling prongs or means 182, 184 (FIG. 11) that are received in the generally U-shaped openings defined by the generally U-shaped walls 140a and 140b, respectively. In the illustration being described, when the guide sleeve 172 is rotated, the plurality of forks, aligning guides, coupling prongs or means 182, 184 are adapted to enable a rotational force or torque to be applied to the screw element 112 in order to screw it into the first and second bones 114 and 116.

As best illustrated in FIG. 12, note that the introducer or inserter tool 166 comprises the outer sleeve 168 that threadably engages the screw element 112 and holds it in the introducer or inserter tool 166 during insertion. Note that a tip or end 185 of guide sleeve 172 is received in the aperture and inside inner wall 112a1 (FIG. 9) of end 112a. This enables the aperture or bore 176 to be in communication with the opening or aperture 144 and the biological material receiving area, hollow area or bore 120 so that when the biological material BM is introduced into the aperture or bore 176, it is guided through the guide sleeve 172 of the introducer or inserter tool 166 and into the biological material receiving area, hollow area or bore 120 of screw element 112. It should be understood that the biological material BM may be loaded into the screw element 112 outside of the patient or may be loaded into the screw element 112 after the screw element 112 is partially or fully positioned and screwed into the first and second bones 114 and 116. Alternatively, a portion of biological material BM may be inserted into the biological material receiving area, hollow area or bore 120 before or after the introducer or inserter tool 166 is mounted onto the generally cylindrical body or core 118, but preferably it is inserted after the screw element 112 has been mounted and fixed in the patient and the tool 166 is mounted to the screw element 112. Note that the aperture or bore 176 in the introducer or inserter tool 166 traverses its entire length and is sized and adapted to introduce the biological material BM into the biological material receiving area, hollow area or bore 120.

Advantageously, the tool 166 provides the function of not only rotatably driving the screw element 112, but also providing an apparatus and means for inserting the biological material BM into the biological material receiving area, hollow area or bore 120 of the generally cylindrical body or core 118. The tool 166 is, therefore, adapted to permit placement and screwing of the generally cylindrical body or core 118 in at least one or a plurality of the first bone 114 or second bone 116 and insertion of the biological material BM into the biological material receiving area, hollow area or bore 120 percutaneously through a single incision in a patient's skin. This provides for a desired minimally invasive surgery. It should be understood, however, that multiple incisions may be used as well. Devices of the past did permit percutaneous insertion of an implant, and they did not permit percutaneous insertion of the biologic into the implant, unlike the embodiments being described herein.

In order to further facilitate insertion or even packing of the biological material BM into the biological material receiving area, hollow area or bore 120, the surgical screw implant system 110 may further comprise a rod or ramrod 186 having an engaging or ramming end 188 and a handle 190 as shown in FIGS. 10 and 12. As illustrated in FIG. 12, the ram or ramrod 186 has a diameter that is slightly smaller than the diameter of the inner wall 174 and therefore can be inserted therein to force any biological material BM in the aperture 176 downward (as viewed in FIG. 12) and into the biological material receiving area, hollow area or bore 120 whereupon it may be packed. This ramming action facilitates forcing the biological material BM into the generally cylindrical body or core 118 so that at least some of the biological material BM can pass and/or into the biological material receiving area, hollow area or bore 120 of the generally cylindrical body or core 118 and through at least one or a plurality of windows or apertures 154 and apertures 142 and 144. As mentioned earlier, the biological material BM may be placed in the generally cylindrical body or core 118 either before or after the screw is screwed into the first and second bones 114 and 116, but preferably is inserted after the screw is mounted in the patient.

Referring now to another embodiment, a screw 200 is shown having a continuous flight or thread 202 (FIG. 23). As with the prior embodiments, the screw 200 comprises a wall 204 that defines a continuous lumen 206 that extends the longitudinal length of the screw 200. The screw 200 comprises a head area 200a having a plurality of generally U-shaped walls 208 that define a plurality of female slots 210. In the illustration being described, the slots 210 are situated approximately 120 degrees apart and are adapted to receive a tool 212 (FIG. 22) having an end 212a for rotatably driving the screw 200. This embodiment also comprises a plurality of interior walls 214 that, like prior embodiments, define a plurality of windows 216 as shown. Thus, it should be appreciated that, like prior embodiments, a body 201 of the screw 200 is fenestrated and comprises at least one or a plurality of windows which could have one or more of the features described earlier herein relative to the previous embodiments. Again, the windows 216 could also be adapted in shape as referred to in prior embodiments, such as the embodiments shown in FIGS. 15-20B. Note that the screw 200 in the illustration shown in FIGS. 21-23 comprises the continuous thread or flight 202 that extends the longitudinal length of the outer surface 218 of the screw 200. Although not shown, it should be appreciated that this embodiment could also comprise an interrupted thread or multiple threads of different pitches and have one or more of the features described earlier herein relative to the embodiments of FIGS. 1-20.

Another feature of the embodiment illustrated in FIGS. 21-23 is that the screw 200 comprises an anti-rotation device surface or stop 220. In the illustration being described, the anti-rotation device surface or stop 220 comprises a plurality of unidirectional teeth or barbs which prevent backout or rotation of the screw 200 once it is screwed into bone. A unique feature of this embodiment is that at least a portion of the walls 214 that define the plurality of apertures or windows 216 are in continuity with the unidirectional teeth or barbs to increase the anti-backout surface. This is illustrated in FIG. 23 wherein it should be noted that the anti-backout barbs or teeth 220, such as the teeth 222, 224 and 226 associated with window 216a are integrally formed with the wall 214a that defines the window 216a.

As best illustrated in FIGS. 22 and 23, note that the screw 200 comprises the thread 202 having a thread diameter that changes during and for each revolution around the axis of the screw 200, including, but not limited to between windows so that the thread 202 has a major diameter DM1 (FIG. 23) that is slightly larger than a minor diameter DM2. An area 223 where the major diameter DM1 and minor diameter DM2 meets, forms or defines a plurality of steps, barbs, shoulders or stop surfaces 228 (FIG. 22). In the illustration being described, the anti-rotation stop surfaces 228 permit rotational movement of the screw 200 in a clock-wise direction, but prevent the screw 200 from rotating in a counter clockwise direction once the screw 200 is placed in the patient.

It should be understood that the minor diameter DM2 is generally situated or begins at an edge, such as edge 216a, associated with wall surface 214a of the plurality of windows or apertures 216. The diameter of the screw thread or flight 202 gets progressively larger until it reaches the major diameter DM1. Note that at the area where the thread 202 reaches the major diameter DM1, the anti-backout shoulders, stops, barbs or teeth coincide and are generally coplanar and in communication with or aligned with the wall 214a of the window 216. Thus, the major diameter DM1 of the screw thread or flight 230 generally becomes aligned with the wall 214a as illustrated and defines a stop surface 225 that has an area that is larger than an area of stop surface 228. Advantageously, this enables the wall 214a to be in communication with the anti-rotation stop surfaces 228 which increases the anti-backout surface. In other words, the wall 214a cooperates with the surface area of the anti-rotation stop surfaces 225 and provides an increased or improved surface area for engaging bone and preventing rotation and backout of the screw 200.

In the illustration being described and when not interrupted by the plurality of windows or apertures 216, the screw thread or flight 230 is uninterrupted and comprises a plurality of anti-rotation stop surfaces 228 that are situated approximately 120 degrees apart for each revolution about the axis of the screw 200. It should be understood that more or fewer of the anti-rotation stop surfaces 228 could be provided if desired.

Also, note that the anti-rotation surfaces, shoulders, stops or barbs, such as surfaces 225 and 228, are generally planar and are generally perpendicular to the screw flight or thread 202 and lie in an imaginary plane(s) that are generally parallel to an axis of the screw 200. The surfaces 225 and 228 are generally planar and are co-planar and lie in a common imaginary plane. The surfaces 225 of the shoulders, barbs or teeth that are adjacent a window area 216, such as the shoulders, barbs or teeth 222, 224 and 226, are also generally co-planar with at least a portion, such as wall 214a, of the wall 214. As mentioned earlier, this enables the combined surface areas of the teeth and the wall 214 to engage bone to provide increased purchase and ant-rotation and backout of the screw. It should be understood, however, that the shoulders, stops or barbs 228 also facilitate anti-rotation or backout. The imaginary planes in which that the shoulders, stops or barbs 225 and 228 lie is generally parallel to an axis of the screw 200 and generally perpendicular to the thread 202 axis.

During use, the following steps of using the system 110 may be performed by a surgeon:
    making an incision in a patient's skin;
    inserting the screw system 110 through the incision so that in traverses the joint 117 or intersection between the first and second bones 114, 116;
    using the tool 166 for rotatably driving the screw element 112 into the first bone 114 and the second bone 116 to fix them together;
    inserting biological material BM into the tool before withdrawing the tool 166 after the using step; and
    driving the biological material BM through the tool sleeve 172 and into the screw element 112 (e.g., by use of the ramrod 186) so that the biological material BM can engage the first and second bones 114, 116 or the joint 117 or intersection so that the biological material BM can develop into a fusion mass across the joint 117 or intersection, thereby fusing the first and second bones 114, 116 together.

Advantageously, the surgical implant system comprises a screw element which, in its preferred embodiment, is percutaneously placed into the facet or other joints of adjacent vertebra. The screw element 112 further comprises a hollow and fenestrated core for the placement of biological material BM for the promotion of osteosynthesis. The system further comprises a detachable instrument tool 166 or means to drive said screw element 112 and inject biological material into the facet joint and screw element 112 via said fenestrated core. The introducer/inserter tool 166 or component functions as both a screwdriver and means for placement of biologic material BM into the lumen of the screw. The tip of this component has a coupling means to transmit torque to the screw for insertion. The introducer/inserter component further comprises the central bore 176 which is contiguous with the fenestrated lumen of the screw component. This central bore 176 allows for the injection of the osteobiologic or biologic material BM to promote fusion. This material then enters the screw component and extrudes through the aperture 144 of screw tip 112b and lateral fenestrations or windows 154 to create a contiguous fusion zone incorporating the adjacent facet bodies.

While the system, apparatus and method herein described constitute preferred embodiments of this invention, it is to be understood that the invention is not limited to this precise system, apparatus and method, and that changes may be made therein without departing from the scope of the invention which is defined in the appended claims.

What is claimed is:

1. A surgical implant system comprising:
a screw element having at least one thread adapted to fix a first bone and a second bone together;
said screw element comprising a core having an inner wall that defines a hollow area and an outer wall having at least one threaded zone, wherein said hollow area is adapted to receive a biological material and provide a fusion mass traversing across a joint and in fusion with each of said first bone and said second bone;
said core being fenestrated with at least one window; and
said core being adapted to receive biological material for the promotion of osteosynthesis or fusing of said first bone and said second bone and for permitting said biological material to pass through said at least one window;
a buttressing head integrally formed at a tool-receiving end of said screw element and being dimensioned to be larger in diameter than said at least one thread to provide external buttressing as said screw element is screwed into bone, said tool-receiving end comprising a tool attachment zone adjacent said buttressing head, said tool attachment zone adapted to be secured to an introducer or inserter tool;
wherein said at least one thread comprises a first thread having a first thread pitch, a second thread having a second thread pitch and an intermediate portion coupling said first and second threads;
said implant system further comprising an introducer or inserter tool, said introducer or inserter tool comprising:
a generally cylindrical body having a first end adapted to be secured to said tool attachment zone and a second end;
said generally cylindrical body comprising an aperture or bore therethrough adapted to permit biological material to be passed therethrough and into said hollow area of said screw element;
wherein the first end of said introducer or inserter tool comprises at least one engaging surface for (i) engaging said tool attachment zone and applying a torque or rotational force to the screw element to screw the screw element into bone, (ii) causing an alignment of said aperture or bore of said introducer or inserter tool and said hollow area of said screw element so that said biological material may be passed through said bore and into said hollow area, and (iii) fixing said introducer or inserter tool to said screw element.

2. The surgical implant system as recited in claim 1 wherein said inner wall is generally cylindrical.

3. The surgical implant system as recited in claim 1 wherein said core comprises a plurality of windows in communication with said hollow area.

4. The surgical implant system as recited in claim 3 wherein said plurality of windows are spaced circumferentially about an axis of said core.

5. The surgical implant system as recited in claim 3 wherein said plurality of windows are spaced longitudinally about an axis of said core.

6. The surgical implant system as recited in claim 3 wherein said core is circular and said plurality of windows are staggered or spaced longitudinally and circumferentially about an axis of said core.

7. The surgical implant system as recited in claim 3 wherein said core comprises said first thread having said first thread pitch, said second thread having said second thread pitch,
a plurality of said plurality of windows traversing through at least one of said first or second threads.

8. The surgical implant system as recited in claim 7 wherein said first and second thread pitches are different.

9. The surgical implant system as recited in claim 3 wherein said core comprises said first thread having said first thread pitch, said second thread having said second thread pitch,
a plurality of said plurality of windows traversing through both of said first or second threads.

10. The surgical implant system as recited in claim 3 wherein each of said plurality of windows are sized to permit said biological material to be extruded therefrom so that it may contact and fuse with bone situated outside said plurality of windows.

11. The surgical implant system as recited in claim 3 wherein said plurality of windows are generally the same shape and size.

12. The surgical implant system as recited in claim 3 wherein said plurality of windows are arranged in a predetermined pattern.

13. The surgical implant system as recited in claim 12 wherein said plurality of windows are arranged in a predetermined pattern, wherein the predetermined pattern is adapted to cause said plurality of apertures to be spaced evenly.

14. The surgical implant system as recited in claim 12 wherein said plurality of windows are arranged in a predetermined pattern, wherein the predetermined pattern is adapted to cause said plurality of apertures to be spaced substantially randomly or unevenly.

15. The surgical implant system as recited in claim 3 wherein said plurality of windows have different shapes.

16. The surgical implant system as recited in claim 3 wherein said plurality of windows have different sizes.

17. The surgical implant system as recited in claim 3 wherein said plurality of windows have at least one of a circular, elliptical, polygonal, rectangular, square or elongated shape.

18. The surgical implant system as recited in claim 1 wherein said screw element is adapted to fix said first bone to said second bone and simultaneously to fuse said first and second bones together.

19. The surgical implant system as recited in claim 1 wherein said core is circular in cross section.

20. The surgical implant system as recited in claim 1 wherein said core comprises said tool-receiving end and a bone-engaging end, said tool-receiving end comprising a first opening that is in communication with said hollow area after said introducer or inserter tool is mounted on said screw element.

21. The surgical implant system as recited in claim 20 wherein said core comprises a tool-receiving end and a screw tip, said screw tip comprising a second opening that is in communication with said hollow area.

22. The surgical implant system as recited in claim 1 wherein said core comprises said tool-receiving end and a screw tip, said screw tip comprising a second opening that is in communication with said hollow area after said introducer or inserter tool is mounted on said screw element.

23. The surgical implant system as recited in claim 1 wherein said first and second thread pitches are different.

24. The surgical implant system as recited in claim 1 wherein said first thread pitch is smaller than said second thread pitch.

25. The surgical implant system as recited in claim 1 wherein said core comprises third threads at said tool attachment zone to allow for engagement of a tool locking sleeve.

26. The surgical implant system as recited in claim 25 wherein said third threads have a handedness that is opposite the handedness of each of the first and second threads.

27. The surgical screw implant as recited in claim 1 wherein said first thread pitch and said second thread pitch are different so that said first thread may threadably engage and drive a first bone to be fused at a first rate and said second thread may threadably engage and drive a second bone to be fused toward said first bone at a second rate, wherein said second rate is greater than said first rate.

28. The surgical implant system as recited in claim 27 wherein said first thread is a proximal thread and said second threads are distal threads, said first thread and said second threads driving said first bone and second bone, respectively, towards said buttressing head at different rates.

29. The surgical implant system as recited in claim 1 wherein said at least one aperture traverses laterally or along a radial line and through said at least one threaded zone.

30. The surgical implant system as recited in claim 1 wherein said hollow area extends along a longitudinal axis of said core.

31. The surgical implant system as recited in claim 1 wherein said hollow area extends through an entire length of said core.

32. The surgical implant system as recited in claim 1 wherein said hollow area defines a lumen in said core.

33. The surgical implant system as recited in claim 1 wherein an intersection between said first and second bones defines a facet joint, said core being adapted to screw into said first and second bones to fix them together and permit biological material in said hollow area to also fuse said first and second bones together.

34. The surgical implant system as recited in claim 1 wherein said introducer or inserter tool is adapted to permit placement or screwing of said screw element in at least one of said first bone or said second bone and insertion of biological material into said hollow area percutaneously through a single incision in a patient's skin.

35. The surgical implant system as recited in claim 1 wherein said introducer or inserter tool further comprises a ramrod or rod for ramming, guiding, injecting or packing said biological material through said tool and into said hollow area.

36. The surgical implant system as recited in claim 35 wherein said ramrod or rod comprises a handle and a generally cylindrical elongated portion having a diameter that is smaller than a diameter of said inner wall so that it can be slidably received therein.

37. The surgical implant system as recited in claim 1 wherein said hollow area extends through said core, said at least one window and said hollow area being adapted so that biological material may be injected into a joint.

38. The surgical implant system as recited in claim 1 wherein said outer wall comprises an anti-rotation device for facilitating preventing the screw element from unscrewing after insertion into the patient.

39. The surgical implant system as recited in claim 38 wherein said anti-rotation device comprises at least one of a shoulder, stops or barbs.

40. The surgical implant system as recited in claim 38 wherein said anti-rotation device is integral with a screw flight that defines said at least one threaded zone.

41. The surgical implant system as recited in claim 38 wherein said anti-rotation device comprises a plurality of shoulders, stops or barbs that lie in imaginary planes that are generally parallel to an axis of said screw element.

42. The surgical implant system as recited in claim 41 wherein said at least one window is defined by a wall surface in said core;
a plurality of said plurality of shoulders stops or barbs define a surface that is coplanar with said wall surface.

43. The surgical implant system as recited in claim 38 wherein said screw element has a male thread, said anti-rotation device being defined by a shoulder, stop or barb at an area of said male thread where a diameter of said male thread changes.

44. The surgical implant system as recited in claim 43 wherein said anti-rotation device comprises a plurality of shoulders, stops or barbs that are spaced along a screw flight of said screw element so that they lie in at least one common imaginary plane with respect to a longitudinal axis of said screw element.

45. The surgical implant system as recited in claim 44 wherein said at least one common imaginary plane is coplanar with a surface or wall that at least partially defines said at least one window.

46. The surgical implant system as recited in claim 44 wherein said plurality of shoulders, stops or barbs lie in three radial planes that are spaced 120 degrees apart, the generally planar surfaces lying in at least one of said radial planes or parallel thereto.

* * * * *